United States Patent
Morizumi et al.

(10) Patent No.: US 12,119,121 B2
(45) Date of Patent: *Oct. 15, 2024

(54) SYSTEM AND METHOD FOR MANAGING FACILITIES

(71) Applicant: ASAHI KASEI KABUSHIKI KAISHA, Tokyo (JP)

(72) Inventors: Masahiro Morizumi, Menlo Park, CA (US); Takafumi Honjo, Tokyo (JP); Hayato Yabuki, Tokyo (JP); Hiroyuki Hirakawa, Tokyo (JP)

(73) Assignee: ASAHI KASEI KABUSHIKI KAISHA, Tokyo (JP)

( * ) Notice: Subject to any disclaimer, the term of this patent is extended or adjusted under 35 U.S.C. 154(b) by 237 days.

This patent is subject to a terminal disclaimer.

(21) Appl. No.: 17/366,318

(22) Filed: Jul. 2, 2021

(65) Prior Publication Data

US 2022/0005609 A1 Jan. 6, 2022

Related U.S. Application Data

(63) Continuation-in-part of application No. 16/920,330, filed on Jul. 2, 2020, now Pat. No. 11,104,347.

(51) Int. Cl.
*G16H 50/80* (2018.01)
*G16H 50/20* (2018.01)
*G16H 50/30* (2018.01)

(52) U.S. Cl.
CPC ............. *G16H 50/80* (2018.01); *G16H 50/20* (2018.01); *G16H 50/30* (2018.01)

(58) Field of Classification Search
CPC ........ G16H 50/80; G16H 50/20; G16H 50/30; G16H 40/67; G08G 1/22; G08G 1/20; G06Q 10/0635; G06Q 50/30
See application file for complete search history.

(56) References Cited

U.S. PATENT DOCUMENTS

| 7,177,738 B2 | 2/2007 | Diaz |
| 10,219,750 B2 | 3/2019 | Duan et al. |

(Continued)

FOREIGN PATENT DOCUMENTS

| JP | 2011140271 A | 7/2011 |
| JP | 2012173862 A | 9/2012 |

(Continued)

OTHER PUBLICATIONS

Sep. 21, 2021, International Search Report and Written Opinion of the International Searching Authority issued in the International Patent Application No. PCT/JP2021/025202.

(Continued)

*Primary Examiner* — Ryan W Sherwin
(74) *Attorney, Agent, or Firm* — KENJA IP LAW PC

(57) ABSTRACT

A system for managing facilities comprises an acoustic event detector including an acoustic sensor for detecting an acoustic event in a compartment of a facility, a facility terminal electrically connected to the acoustic event detector, and an external server communicating with the facility terminal via a network. At least one of the facility terminal and the external server comprises a processor. The processor is configured to implement the steps of: extracting a respiratory disease symptom of a user in the facility from the detected acoustic event; assessing the respiratory disease symptom of the user to generate infection risk information associated with an infection risk of a next user expected to use the facility; and transmitting the infection risk information to at least one of an external user terminal, the external server, and a third party via the network. A method for managing facilities is also provided.

21 Claims, 14 Drawing Sheets

(56) References Cited

U.S. PATENT DOCUMENTS

| | | |
|---|---|---|
| 11,087,886 B1* | 8/2021 | Brown .................. G16H 50/80 |
| 11,104,347 B1* | 8/2021 | Morizumi .............. G06Q 50/22 |
| 11,184,739 B1* | 11/2021 | Wellig .................. G16H 50/70 |
| 11,504,011 B1* | 11/2022 | Jain ........................ G16H 10/20 |
| 2015/0100330 A1* | 4/2015 | Shpits .................... G16H 50/80 |
| | | 705/2 |
| 2015/0134369 A1* | 5/2015 | Sakata .............. G09B 19/0084 |
| | | 434/236 |
| 2015/0330817 A1* | 11/2015 | Law ........................ G16Z 99/00 |
| | | 702/19 |
| 2015/0348179 A1 | 12/2015 | Kamisawa |
| 2017/0086778 A1* | 3/2017 | Cahan ...................... A61B 7/02 |
| 2018/0092603 A1* | 4/2018 | Duan .................. G05B 19/042 |
| 2019/0133511 A1 | 5/2019 | Migneco et al. |
| 2019/0148023 A1 | 5/2019 | Sadilek et al. |
| 2019/0237094 A1* | 8/2019 | Kakadiaris .............. G06F 3/165 |
| 2020/0360858 A1 | 11/2020 | Mathur et al. |
| 2021/0012905 A1* | 1/2021 | Yugawa .................. G16H 10/60 |
| 2021/0043330 A1* | 2/2021 | Ikeshima ................ G10L 25/66 |
| 2021/0272702 A1* | 9/2021 | Hakami .................. H04W 4/027 |
| 2022/0129687 A1* | 4/2022 | Munir ...................... G01S 13/46 |
| 2022/0277764 A1* | 9/2022 | Ciliberti ................ G16H 50/20 |

FOREIGN PATENT DOCUMENTS

| | | |
|---|---|---|
| JP | 2018179547 A | 11/2018 |
| JP | 2020008969 A | 1/2020 |
| WO | 2013006618 A2 | 1/2013 |
| WO | 2019003325 A1 | 1/2019 |

OTHER PUBLICATIONS

Dec. 13, 2022, International Preliminary Report on Patentability issued in the International Patent Application No. PCT/JP2021/025202.

\* cited by examiner

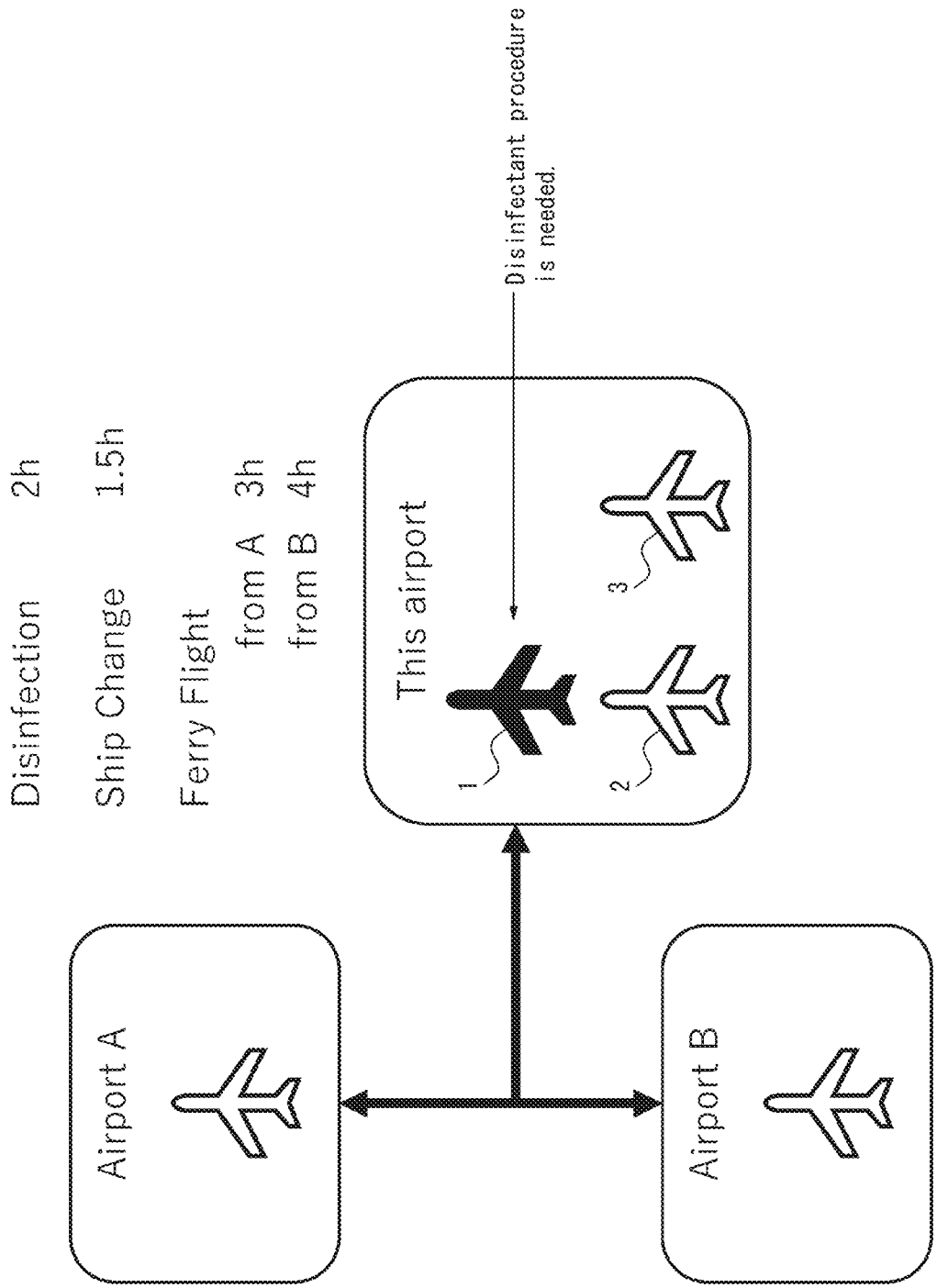

SYSTEM AND METHOD FOR MANAGING FACILITIES

CROSS-REFERENCE TO RELATED APPLICATION

This application is a continuation-in-part application of U.S. application Ser. No. 16/920,330, filed Jul. 2, 2020, and entitled "System and method for managing shared vehicle", which is hereby incorporated by reference herein in its entirety.

TECHNICAL FIELD

The present disclosure relates to a system and method for managing facilities.

BACKGROUND

For businesses involving a fleet of vehicles such as a vehicle rental service and a car sharing service, managing the condition of each vehicle is the key to maximize the usage of the fleet. For example, U.S. Pat. No. 7,177,738 proposes a vehicle management system that is capable of easily obtaining information on the condition and usage of a vehicle, thereby managing the fleet of vehicles with high efficiency and low cost.

These services, however, face a rapidly changing operating environment due to the new coronavirus disease (COVID-19). Both customers and service providers are likely to have significantly increased expectation of hygiene. The service providers need to reassure their customers that they have taken sufficient steps to ensure their safety.

The virus is thought to spread mainly from person-to-person through respiratory droplets produced when an infected person coughs, sneezes, or talks. The Centers for Disease Control and Prevention (CDC) has released guidelines to reduce the risk of exposure to the virus that causes COVID-19. The guidelines encourage the service providers to, at minimum, clean and disinfect frequently touched surfaces in the vehicle.

Recent studies also indicate that the virus can persist in fine particles know as aerosols and survive in the air for several hours. As the aerosols may infect cells throughout that time period, it is ideal to take more thorough cleaning and disinfection procedures if a passenger is suspected to contract the disease. It is, however, hard for the service providers to identify a risk of infection when the vehicle is returned.

SUMMARY

It is, therefore, an object of the present disclosure to provide a system and method for managing shared vehicles that is capable of remotely determine a health condition of a passenger of the vehicle, thereby ensuring the health safety of the next passenger.

In order to achieve the object, one aspect of the present disclosure is a system for managing shared vehicles, the system comprising:
  an acoustic event detector including an acoustic sensor for detecting an acoustic event in a compartment of a vehicle,
  a vehicle terminal electrically connected to the acoustic event detector, and
  an external server communicating with the vehicle terminal via a network,
  wherein at least one of the vehicle terminal and the external server comprises a processor, and
  the processor is configured to implement the steps of:
    extracting a respiratory disease symptom of a passenger in the vehicle from the detected acoustic event;
    assessing the respiratory disease symptom of the passenger to generate infection risk information associated with an infection risk of a next passenger expected to ride the vehicle; and
    transmitting the infection risk information to an external user terminal, the external server, or a third party via the network.

As used herein, the term "vehicle" generally means every device in, upon, or by which any person is transported or drawn, and may be used upon fixed rails, tracks or the like, or in the air or on water. As such vehicle, a motor vehicle, a bus, a train, a cable car, a gondola lift, an amusement ride, an airplane, and a motorboat may be recited by way of example.

The vehicle terminal is a data processing device such as a general-purpose computer, a personal computer, a dedicated computer, a workstation, a PCS (Personal Communications System), a cellular (mobile) telephone, a smart phone, an RFID receiver, a laptop computer, a tablet computer and any other programmable data processing device.

The network is not limited to a particular communication network and may include any communication network including, for example, a mobile communication network and the internet.

The processor may be, but not limited to, a general-purpose processor or a dedicated processor specialized for a specific process. The processor includes a microprocessor, a central processing unit (CPU), an application specific integrated circuit (ASIC), a digital signal processor (DSP), a programmable logic device (PLD), a field programmable gate array (FPGA), a controller, a microcontroller, and any combination thereof.

The respiratory disease symptom includes, but is not limited to, cough, sneeze, breath, sniffle, throat clearing and the like.

In one embodiment, the system may additionally have a position detector such as a GPS (Global Positioning System) receiver for detecting a current position of the vehicle. In this case, the processor may be further configured to implement the step of obtaining at least one of environmental information around the vehicle and infection risk information from a neighboring vehicle via the network, and the step of assessing the respiratory disease of the passenger may be implemented also on the basis of the at least one of environmental information around the vehicle and infection risk information from a neighboring vehicle.

In another embodiment, the processor may be further configured to implement the step of modifying at least one of a communication frequency and information to be transmitted to the external server.

In a further embodiment, the system may also have an air cleaner in the vehicle, and the processor may be further configured to implement the step of controlling the air cleaner on the basis of a frequency of occurrence of the respiratory disease symptom. In addition or alternatively, the system may further have a biological information acquisition unit for acquiring biological information of the passenger, and the processor may be further configured to implement the step of controlling the biological information acquisition unit based on a frequency of occurrence of the respiratory disease symptom.

In yet another embodiment, the processor may be further configured to implement the steps of generating vehicle compartment contamination information indicating a necessity of a disinfectant procedure prior to a next use of the vehicle based on the infection risk information, and transmitting the vehicle compartment contamination information to the external user terminal via the network. In this embodiment, the external server may include a database storing reservation information and status information of the shared vehicles, and may modify the status information of the vehicle to reflect the vehicle compartment contamination information. When the vehicle compartment contamination information indicates that the disinfectant procedure is needed and the reservation information indicates that the vehicle has a reservation, the external server may search another available vehicle and assigns the available vehicle to the reservation. The vehicle compartment contamination information may be updated after the disinfectant procedure is completed so as to indicate that the vehicle is clean.

In a yet further embodiment, the external server may search a potentially contaminated vehicle having a usage history similar to that of the vehicle determined as high infection risk, and may modify at least one of a communication frequency and information to be transmitted to the external server.

Another aspect of the present disclosure is a method for managing shared vehicles, the method comprising the steps of:
detecting an acoustic event in a compartment of a vehicle;
extracting a respiratory disease symptom of a passenger in the vehicle from the detected acoustic event;
assessing the respiratory disease symptom of the passenger to generate infection risk information associated with an infection risk of a next passenger expected to ride the vehicle; and
transmitting the infection risk information to an external user terminal, the external server, or a third party via a network.

The method may further comprise the steps of:
detecting a current position of the vehicle; and
obtaining at least one of environmental information around the vehicle and infection risk information from a neighboring vehicle via the network. In this case, the step of assessing the respiratory disease of the passenger may be implemented also on the basis of the at least one of environmental information around the vehicle and infection risk information from a neighboring vehicle.

The method may further comprise the steps of: modifying at least one of a communication frequency and information to be transmitted to the external server; controlling an air cleaner in the vehicle on the basis of a frequency of occurrence of the respiratory disease symptom; and/or acquiring biological information of the passenger on the basis of a frequency of occurrence of the respiratory disease symptom;

In another embodiment, the method may further comprise the steps of generating vehicle compartment contamination information indicating a necessity of a disinfectant procedure prior to a next use of the vehicle based on the infection risk information; and transmitting the vehicle compartment contamination information to the external user terminal via the network. In addition, the method may further comprise the steps of accessing a database storing reservation information and status information of the shared vehicles; and modifying the status information of the vehicle to reflect the vehicle compartment contamination information. Furthermore, the method may further comprise the step of, when the vehicle compartment contamination information indicates that the disinfectant procedure is needed and the reservation information indicates that the vehicle has a reservation, searching another available vehicle and assigns the available vehicle to the reservation. The method may further comprise the step of updating the vehicle compartment contamination information after the disinfectant procedure is completed so as to indicate that the vehicle is clean.

In a further embodiment, the method may further comprise the step of searching a potentially contaminated vehicle having a usage history similar to that of the vehicle determined as high infection risk, and modifying at least one of a communication frequency and information to be transmitted to the external server.

According to the system and method for managing shared vehicles, it is possible to remotely determine a health condition of a passenger or passengers of the vehicle, thereby ensuring the health safety of the next passenger.

In the description above, the object is assumed to be a "vehicle". The vehicle is therefore described as including a "vehicle terminal". When the object is a "facility", however, the "facility" can be described as including a "facility terminal". Accordingly, the explanation pertaining to the "vehicle" in the case of the object being a "vehicle" also applies to the "facility" in the case of the object being a "facility". Similarly, the explanation pertaining to the "vehicle terminal" in the case of the object being a "vehicle" also applies to the "facility terminal" in the case of the object being a "facility".

Another aspect of the present disclosure is a system for managing facilities, the system comprising:
an acoustic event detector including an acoustic sensor for detecting an acoustic event in a compartment of a facility,
a facility terminal electrically connected to the acoustic event detector, and
an external server communicating with the facility terminal via a network,
wherein at least one of the facility terminal and the external server comprises a processor, and
the processor is configured to implement the steps of:
extracting a respiratory disease symptom of a user in the facility from the detected acoustic event;
assessing the respiratory disease symptom of the user to generate infection risk information associated with an infection risk of a next user expected to use the facility; and
transmitting the infection risk information to at least one of an external user terminal, the external server, and a third party via the network.

In one embodiment, the acoustic sensor may capture acoustic sound, and the processor may be further configured to implement the step of transmitting said acoustic data to at least one of the external user terminal, the external server, and the third party via the network.

In another embodiment, the processor may be further configured to implement the step of delivering an advertisement to at least one of the external server, the facility terminal, the external user terminal, and the third party via the network based on the infection risk information.

Alternatively or additionally, the processor may be configured to implement the step of rating the user based on statement related to physical condition of the user and on the infection risk information for the user.

Alternatively or additionally, the processor may be configured to implement the step of transmitting information indicating the degree of risk of area within the facility to at least one of the external server, the facility terminal, the external user terminal, and the third party via the network based on the infection risk information.

Alternatively or additionally, the processor may be configured to implement the step of transmitting instruction to improve the ventilation status of the facility to at least one of the external server, the facility terminal, the external user terminal, and the third party via the network based on the infection risk information.

Alternatively or additionally, the processor may be configured to implement the step of transmitting countermeasure information to at least one of the external server, the facility terminal, the external user terminal, and the third party via the network based on the infection risk information.

Alternatively or additionally, the processor may be configured to implement the step of modifying at least one of a communication frequency and information to be transmitted to at least one of the external server, the facility terminal, the external user terminal, and the third party via the network.

In one embodiment, the system may further comprise an air cleaner in the facility, wherein the processor is further configured to implement the step of controlling the air cleaner on the basis of a frequency of occurrence of the respiratory disease symptom.

In another embodiment, the processor is further configured to implement the steps of generating facility compartment contamination information indicating a necessity of a disinfectant procedure prior to a next use of the facility based on the infection risk information, and transmitting the facility compartment contamination information to at least one of the external server, the facility terminal, the external user terminal, and the third party via the network.

The external server may search a potentially contaminated facility having a usage history similar to that of the facility determined as high infection risk, and modifies at least one of a communication frequency and information to be transmitted to at least one of the external server, the facility terminal, the external user terminal, and the third party via the network.

Yet another aspect of the present disclosure is a method for managing facilities, the method comprising the steps of:
  detecting an acoustic event in a compartment of a facility;
  extracting a respiratory disease symptom of a user in the facility from the detected acoustic event;
  assessing the respiratory disease symptom of the passenger to generate infection risk information associated with an infection risk of a next passenger expected to ride the facility; and
  transmitting the infection risk information to at least one of an external user terminal, the external server, and a third party via the network.

The method may further comprise the step of transmitting the acoustic data to at least one of the external user terminal, the external server, and the third party via the network.

The method may further comprise the step of delivering an advertisement to at least one of the external server, the facility terminal, the external user terminal, and the third party via the network based on the infection risk information.

The method may further comprise the step of rating the user based on statement related to physical condition of the user and on the infection risk information for the user.

The method may further comprise the step of transmitting information indicating the degree of risk of area within the facility to at least one of the external server, the facility terminal, the external user terminal, and the third party via the network based on the infection risk information.

The method may further comprise the step of transmitting instruction to improve the ventilation status of the facility to at least one of the external server, the facility terminal, the external user terminal, and the third party via the network based on the infection risk information.

The method may further comprise the step of transmitting countermeasure information to at least one of the external server, the facility terminal, the external user terminal, and the third party via the network based on the infection risk information.

The method may further comprise the step of modifying at least one of a communication frequency and information to be transmitted to at least one of the external server, the facility terminal, the external user terminal, and the third party via the network.

The method may further comprise the step of controlling an air cleaner on the basis of a frequency of occurrence of the respiratory disease symptom.

The method may further comprise the steps of generating facility compartment contamination information indicating a necessity of a disinfectant procedure prior to a next use of the facility based on the infection risk information, and transmitting the facility compartment contamination information to at least one of the external server, the facility terminal, the external user terminal, and the third party via the network.

The method may further comprise the steps of searching a potentially contaminated facility having a usage history similar to that of the facility determined as high infection risk, and modifying at least one of a communication frequency and information to be transmitted to at least one of the external server, the facility terminal, the external user terminal, and the third party via the network.

These and other aspects may be understood more readily from the following description and the appended drawings.

BRIEF DESCRIPTION OF THE DRAWINGS

Various other objects, features and attendant advantages of the present invention will become fully appreciated as the same becomes better understood when considered in conjunction with the accompanying drawings, in which like reference characters designate the same or similar parts throughout the several views, and wherein:

FIG. 14 illustrates an example of processing for an airplane with a high infection risk in the system according to the present embodiment.

DETAILED DESCRIPTION

Figure 1:
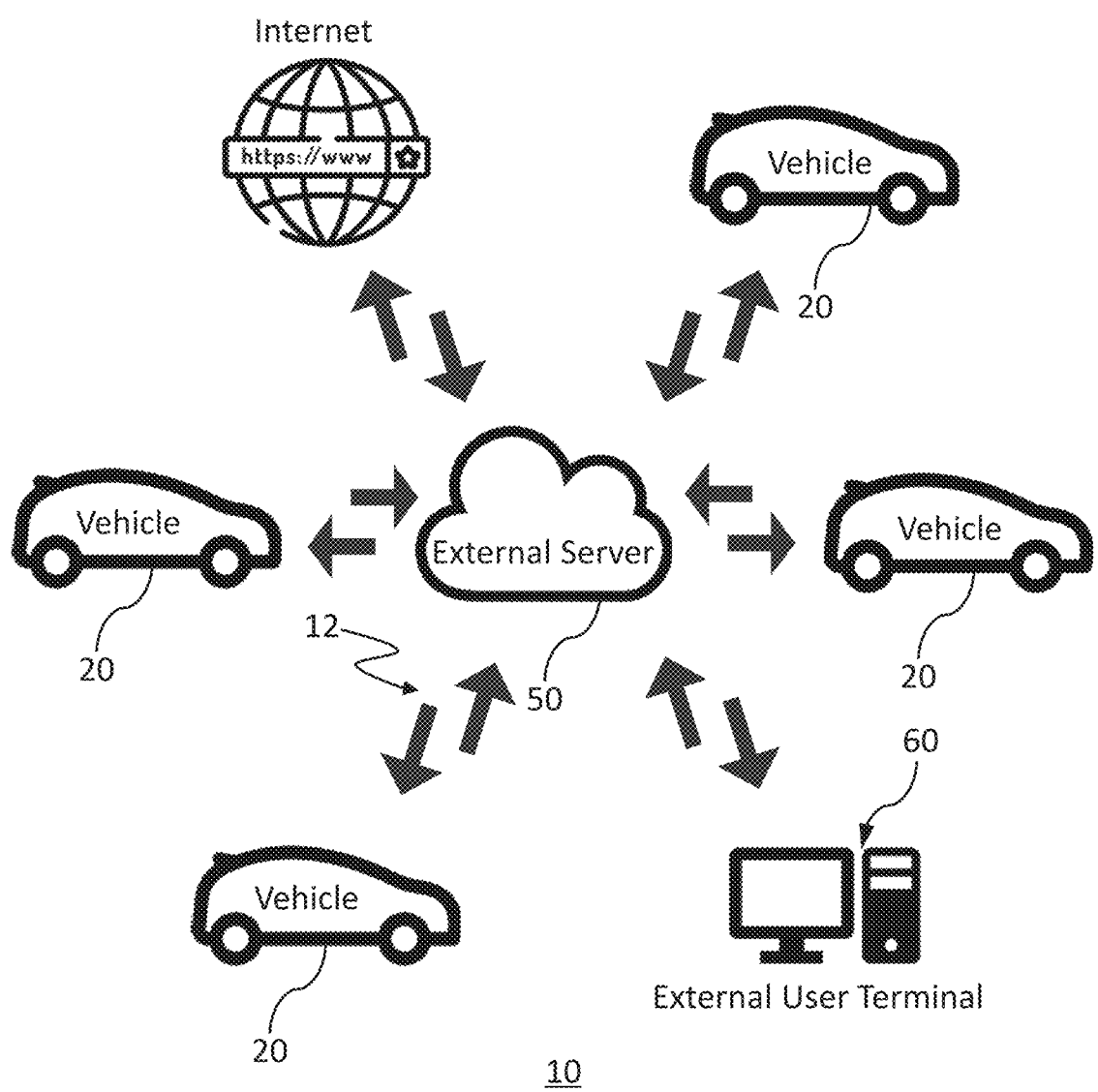
FIG. 1 is a schematic diagram of a system for managing shared vehicles according to an embodiment of the present disclosure.
Figure 2:
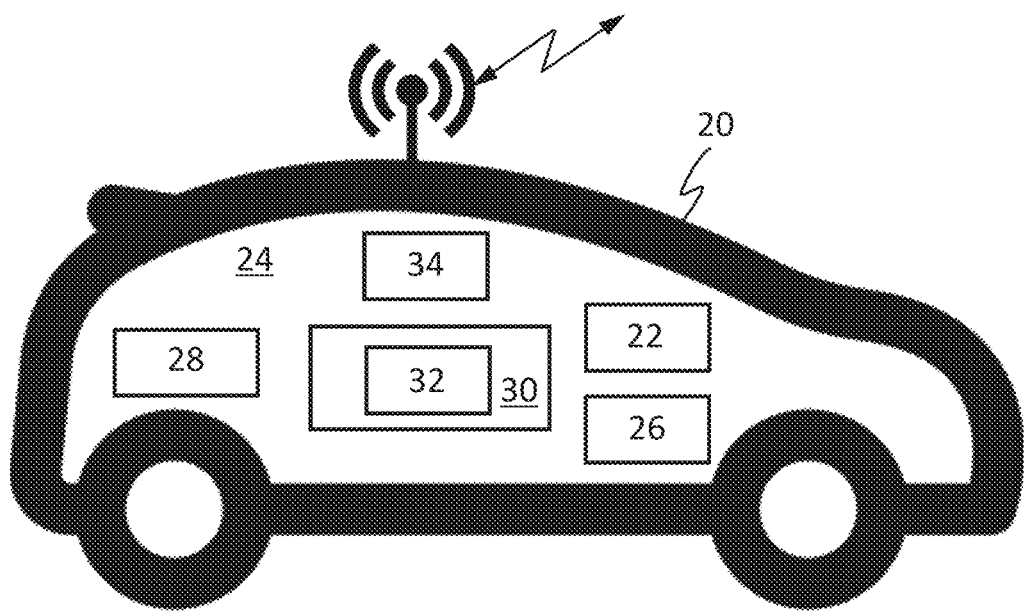
FIG. 2 is a schematic diagram of a part of the system mounted on a vehicle.

Embodiments will now be described with reference to the accompanying drawings. FIG. 1 is a schematic diagram of a schematic diagram of a system for managing shared vehicles according to an embodiment of the present disclosure, and FIG. 2 is a schematic diagram of a part of the system mounted on a vehicle.

A system 10 is designed for managing shared vehicles 20. Each vehicle 20 has an acoustic event detector 22 which includes an acoustic sensor for detecting an acoustic event in a compartment 24 of a vehicle 20. The acoustic sensor may be any type of a sensor, such as a microphone, that converts a sound signal (e.g., sound wave) into a voltage or current proportional to the detected signal. The acoustic sensor may include an electrostatic sensor or piezoelectric sensor (e.g., high frequency ultrasonic sound sensor) that detects sound pressure waves within the ultrasound range. More than one acoustic sensors may be used depending on, for example, the size, capacity and design of the compartment 24. The acoustic sensor may be dedicated to the system 10, but a microphone provided for another system such as a navigation system, a communication system, or an audio system may also be used. The acoustic sensor may be connected to the acoustic event detector 22 in a wired or wireless manner. A cellular phone may also serve as the acoustic sensor via a wireless connection such as Bluetooth.

A vehicle terminal 30 is also provided in the vehicle 20 and electrically connected to the acoustic event detector 22. An external server 50 located at a remote site such as a data center communicates with the vehicle terminal 30 and an external user terminal 60 via a network 12.

The system 10 also has a processor 32 for processing and analyzing the acoustic event detected by the acoustic event detector 22. The processor 32 may be provided in the vehicle terminal 30, the external server 50 or both of them. In the embodiment shown in FIG. 2, the processor 32 is provided in the vehicle terminal 30. The vehicle 20 is also equipped with a biological information acquisition unit 26, an air cleaner 28, and a position detector 34, which will be discussed below. One or more sensors (not shown) may be provided for measuring the air quality, the temperature, the humidity and the like inside and/or outside the vehicle 20.

Figure 3:
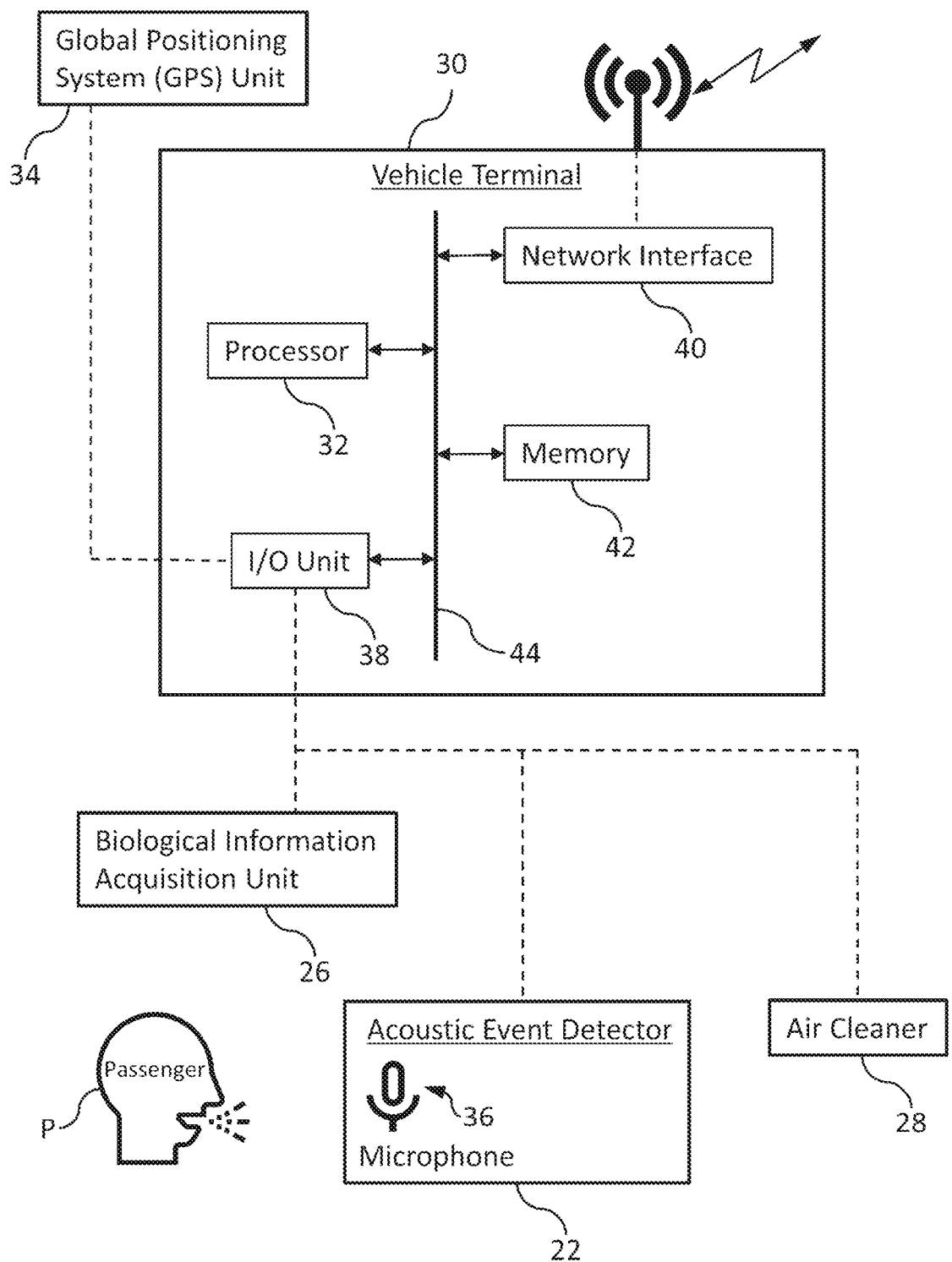
FIG. 3 is a block diagram showing the part of the system mounted on the vehicle.

FIG. 3 is a block diagram showing the part of the shared vehicles managing system 10 mounted on the vehicle 20. The acoustic event detector 22 has a microphone 36 as an acoustic sensor for capturing acoustic sounds and detecting an acoustic event produced by a passenger P in the compartment 24. The microphone 36 may be integrated in the acoustic event detector 22 itself, or may be a stand-alone type and coupled to the acoustic event detector 22 in a wired or wireless manner. In either event, the acoustic event detector 22 receives the captured acoustic sounds as electric signals from the microphone 36 and processes the electric signals, for example, by subjecting the electric signals to an analog-to-digital conversion to generate acoustic data.

The vehicle terminal 30 communicates with other units mounted in the vehicle 20, such as the acoustic event detector 22, the biological information acquisition unit 26, the air cleaner 28, and the position detector (GPS unit) 34 via an I/O (Input/Output) unit 38. The vehicle terminal 30 also communicates with the external server 50 via a network interface 40. The network interface may include a communication module compatible with mobile communication standards such as 4th Generation (4G) and 5th Generation (5G). The communication network may be an ad hoc network, a local area network (LAN), a metropolitan area network (MAN), a wireless personal area network (WPAN), a public switched telephone network (PSTN), a terrestrial wireless network, an optical network, or any combination thereof. The vehicle terminal 30 also includes a memory 42 which may function as, for example, a main storage device, a supplemental storage device, or a cache memory. The memory 42 stores any information used for the operation of the vehicle terminal 30. For example, the memory 42 may store a system program, an application program, data from the other units, data to be sent to the external server 50, data acquired from the external server 50 and so on. The information stored in the memory 42 may be updatable by, for example, information acquired from the external server 50 by the network interface 40. The memory 42 may be, for example, a semiconductor memory, a magnetic memory, or an optical memory. The memory 42 is not particularly limited to these, and may include any of long-term storage, short-term storage, volatile, non-volatile and other memories. Further, the number of memory modules serving as the memory 42 and the type of medium on which information is stored are not limited. The processor 32, the I/O unit 38, the network interface 40 and the memory 42 are electrically connected with each other via a bus 44.

Figure 4:
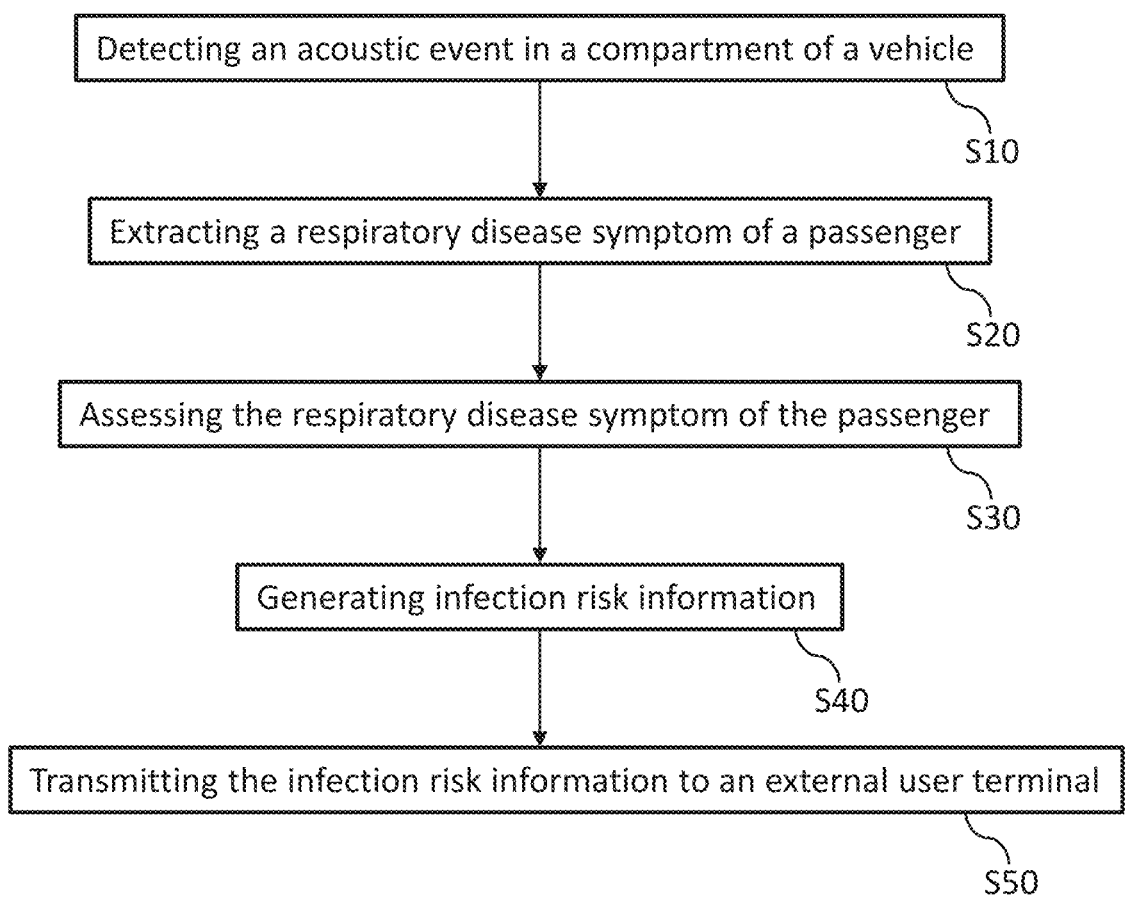
FIG. 4 is a flowchart showing steps implemented by the vehicle terminal according to another embodiment of the present disclosure.

Referring now to FIG. 4, the operation of the shared vehicles managing system 10 will be discussed.

At the step S10, the microphone 36 of the acoustic event detector 22 captures environmental sounds including sounds produced by the passenger P in the compartment 24 and converts the sound into the acoustic data. Then, the acoustic data is transferred to an I/O (input/output) unit 38 of the vehicle terminal 30.

The processor 32 extracts, at the step S20, a respiratory disease symptom of the passenger P from the acoustic data. For example, filtering or other types of frequency and/or amplitude analysis may be used to identify distinctive features of the captured acoustic data, or to remove extraneous (e.g., background) noise components from the acoustic data. The processor 32 further processes the distinctive features, for example, by comparing attributes of the features to a lookup table, database, or other data organization structure stored in the memory 42, thereby identifying the respiratory disease symptom. The respiratory disease symptom may include, for example, the coughing, the sneezing, the wheezing, the sniffing, the throat clearing, the nasally voice, the shallow breathes and the deep breathes. A model or algorithm used for extracting the respiratory disease symptom may be modified by the passenger's personal characteristics such as age, sex, race and anamnesis to enhance the accuracy of the extraction. Machine learning may be used to build and improve the model or algorithm. Alternatively, the model or algorithm may be updated via the network.

Figure 9:
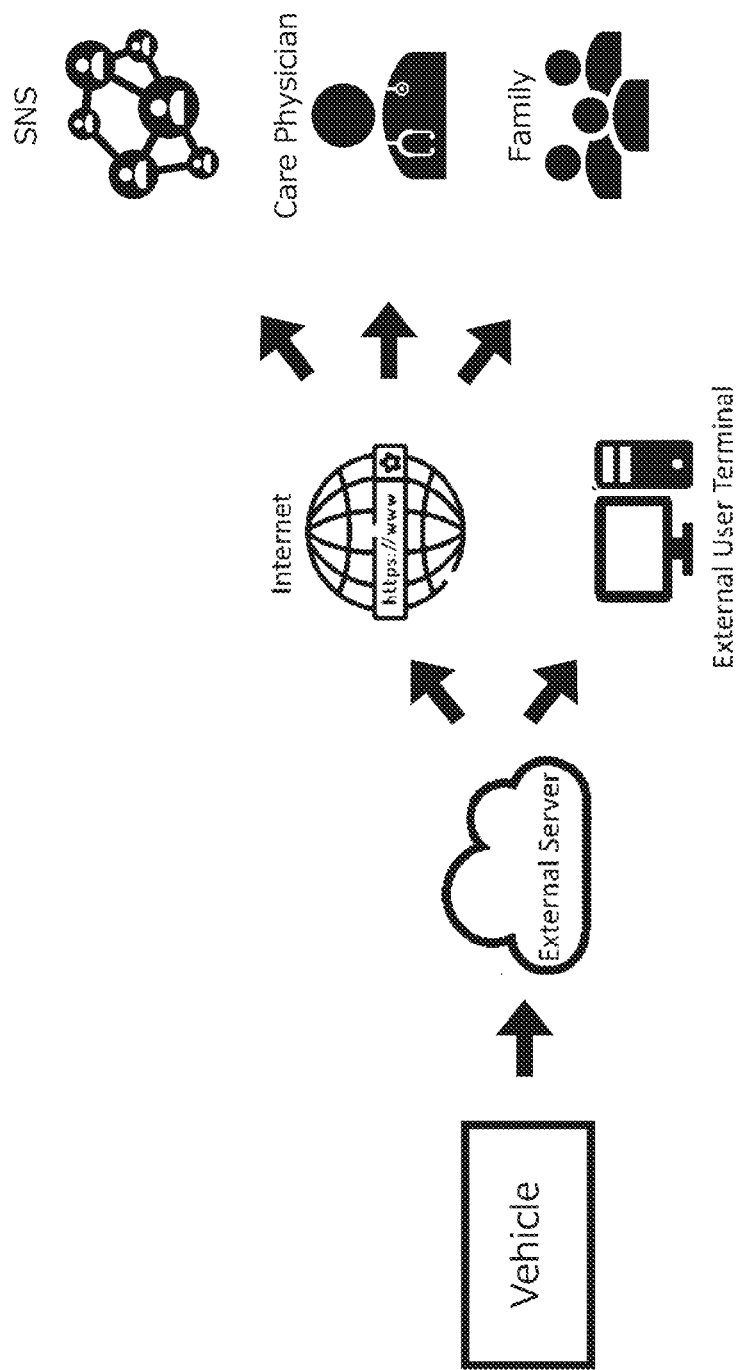
FIG. 9 illustrates an example of acoustic data being transmitted in the system according to the present embodiment.

At the step S20, when detecting a respiratory disease symptom of the passenger from the acoustic data, such as the sound of a cough by the user, the processor 32 may transmit the acoustic data to an external destination. For example, as shown in FIG. 9 the processor 32 may transmit the sound of the cough by the user to the user's primary care physician when the user's consent is obtained. For example, as shown in FIG. 9 the processor 32 may upload the sound of the cough by the user to a social networking service (SNS) when the user's consent is obtained.

Specifically, the processor 32 may transmit the acoustic data to an external server based on a distribution list, as shown in FIG. 9. The processor 32 may also transmit the acoustic data to a third-party, via the external server and the Internet, based on a distribution list. The third party is not particularly limited, but examples thereof include an SNS, the user's primary care physician, and the user's family. The processor 32 may also transmit the acoustic data to an external user terminal, via the external server, based on a distribution list.

The external server or the external user terminal may, for example, store the distribution list in a memory or the like mounted in the external server or external user terminal. The distribution list includes information for specifying a recipient, such as the email address of a third party or the URL of a third party. The memory is not necessarily provided internally in the external server or the external user terminal and may be configured to be external to the external server or the external user terminal.

Then, at the step S30, the processor 32 assesses the respiratory disease symptom. For example, the intensity, frequency and duration of the coughing and/or the sneezing may be compared with the lookup table stored in the memory 42 to determine a severity of the symptom. A model or algorithm used for assessing the respiratory disease symptom may be modified by the passenger's personal characteristics such as age, sex, race and anamnesis to enhance the accuracy of the assessment. Machine learning may be used to build and improve the model or algorithm. Alternatively, the model or algorithm may be updated via the network.

At the step S40, the processor 32 generates infection risk information based on the severity of the symptom, and, optionally, other conditions of the vehicle. For example, the number of passengers, the size of the compartment, the air quality and the humidity and the temperature in the compartment may be weighed.

At the step S40, the processor 32 may generate the infection risk information for the user based on the ventilation status of the space in addition to the respiratory disease symptom of the user. Examples of information indicating the ventilation status of the space include information indicating whether the air conditioner is on or off, information indicating the intensity of the air conditioner, information indicating the airflow of the air conditioner, information indicating the operation mode of the air conditioner (such as cool, heat, dehumidifier, eco), information indicating whether air is being recirculated, information indicating the open/close state of windows provided in the space, information indicating the state of airflow in the space, and information indicating the concentration of a gas (such as carbon dioxide) in the space.

For example, when the concentration of carbon dioxide is high, the processor 32 may generate infection risk information for the user indicating a high infection risk for the user. For example, when the concentration of carbon dioxide is low, the processor 32 may generate infection risk information for the user indicating a low infection risk for the user.

The processor 32 transmits, at the step S50, the infection risk information via the network interface 40 over the network to the external server 50. Other information such as a vehicle ID, the number of people having the symptom, and the location of the people having the symptom in the compartment (e.g., front passenger seat, driver seat and the like) may also be transmitted to the external server 50. The external server 50 forwards all or a part of the information to the external user terminal 60. The external user terminal 60 may be placed at, for example, a branch office of the service provider where the vehicle 20 is supposed to be returned. More than one external user terminal 60 are connected to the external server 50. The external server 50 may also forward all or a part of the information to a third party. The vehicle terminal 30 or the external server 50 may forward information to the third party based on a distribution list. Non-limiting examples of "third party" includes a hospital, a terminal at a destination of the vehicle 20, a control device of a display, and a control device of a speaker.

Figure 5:
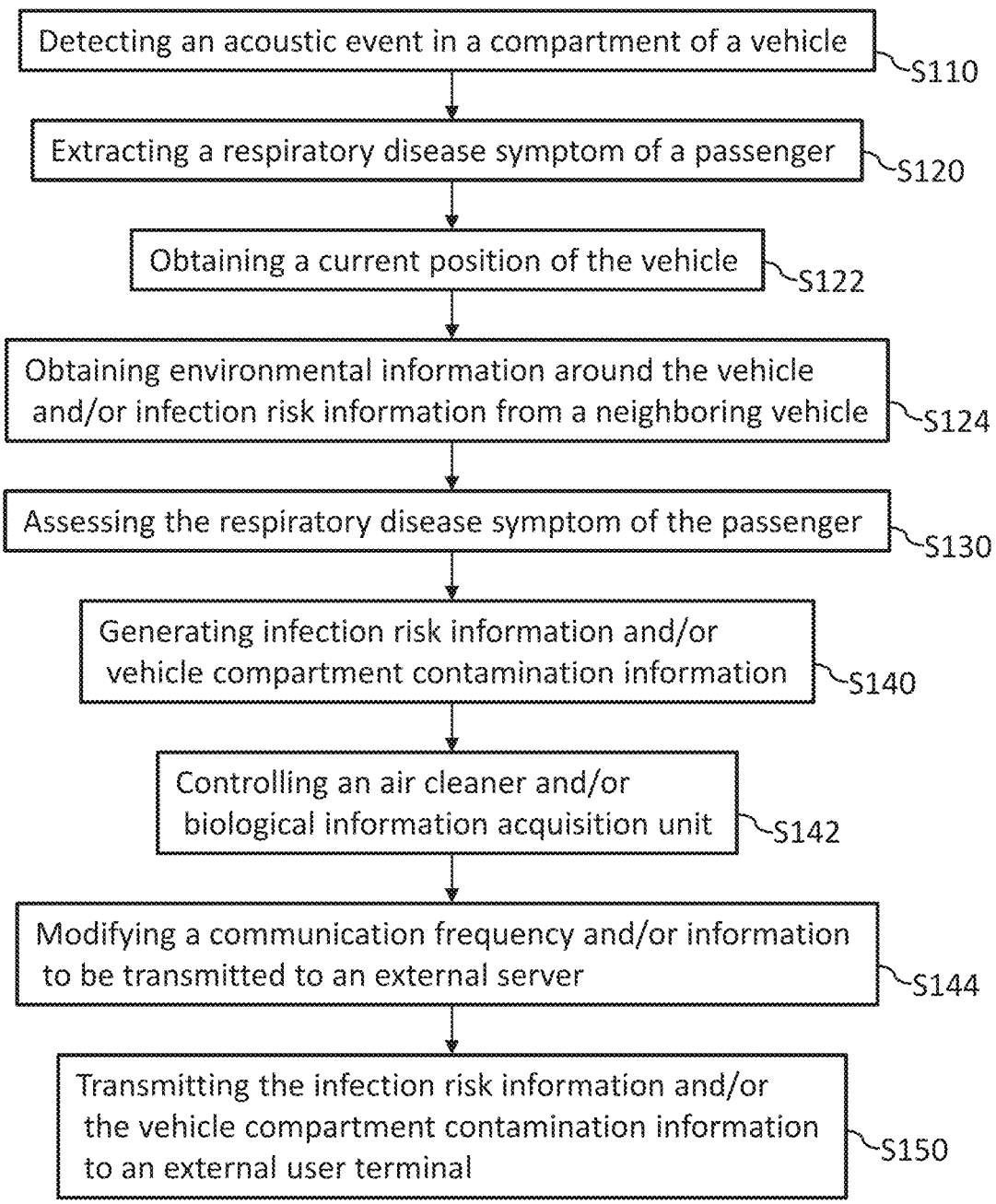
FIG. 5 is a flowchart showing steps implemented by the vehicle terminal according to another embodiment of the present disclosure.

FIG. 5 is a flowchart showing the steps implemented by the vehicle terminal according to another embodiment.

At the step S110, the acoustic event detector 22 captures the environmental sounds which are converted sound into the acoustic data and then transferred to the I/O unit 38. The processor 32 extracts, at the step S120, the respiratory disease symptom of the passenger P from the acoustic data. These steps may be implemented in the similar manner as the steps S10 and S20 discussed above.

At the step S120, when detecting a respiratory disease symptom of the passenger from the acoustic data, such as the sound of a cough by the user, the processor 32 may transmit the acoustic data to an external destination. For example, as shown in FIG. 9 the processor 32 may transmit the sound of the cough by the user to the user's primary care physician when the user's consent is obtained. For example, as shown in FIG. 9 the processor 32 may upload the sound of the cough by the user to a social networking service (SNS) when the user's consent is obtained.

Then, at the step S122, the processor 32 obtains a current position of the vehicle 20 from the GPS unit 34. The GPS unit 34 may be dedicated to the shared vehicle managing system 10, but a GPS unit provided for another system such as a navigation system also be used. A GPS unit integrated in a cellular or smart phone may also serve as the GPS unit 34 via a wireless connection such as Bluetooth.

At the step S124, the processor 32 generates a query including the current position of the vehicle 20 and transfers the query via the network interface 40 to the external server 50 or any other server on the internet. In response, environmental information around the vehicle 20 is sent back from the server. The environmental information may include the weather, the temperature, the humidity, the pressure, the wind velocity, the pollen counts, the air quality index (AQI), the particulate matter (PM) 2.5 and any other information associated with potential and known causes of respiratory diseases. In addition or alternative to the environmental information, the external server 50 searches a vehicle currently or recently driving in the same area (neighboring vehicle) and, if any, sends back the infection risk information obtained from the neighboring vehicle to the processor 32.

The processor 32 assesses, at the step S130, the respiratory disease symptom. In this embodiment, the information obtained via the network (i.e., the environmental information around the vehicle 20 and/or the infection risk information from the neighboring vehicle) is also taken into the assessment of the respiratory disease symptom. For example, when the pollen counts and/or the AQI is high, the processor 32 raise a risk threshold of the frequency of sneezing as there will be a high chance of sneezing due to the pollen or air pollution (i.e., sneezing not related to the respiratory diseases). The external server 50 may also calculate an average frequency of sneezing per person in that area on the bases of information accumulated from the vehicles managed by the external server 50 and send it back to the processor 32. The processor 32 may subtract the average frequency of sneezing from the measured frequency of sneezing of the passenger P and use the subtraction for the assessment.

At the step S140, the processor 32 generates infection risk information based on the severity of the symptom. In addition or as an alternative, contamination information of the vehicle compartment 24 may be generated. The concentration of aerosols (i.e., the level of contamination) in the compartment 24 of the vehicle 20 depends on not only the frequency of respiratory disease symptoms but also the size or capacity of the compartment 24 of the vehicle 20 as well as the duration of the symptoms. Therefore, the vehicle compartment contamination information should be determined with considering these factors as well. That is, the infection risk information indicates a likelihood (risk) of an infection of a next passenger expected to ride the vehicle, while the vehicle compartment contamination information indicates a necessity of a disinfectant procedure after the vehicle is returned and prior to a next use of the vehicle.

When a likelihood of contamination of the compartment is increasing, the processor 32 may activate (if not activated) or turn up (if already activated) the air cleaner 28 as a remediation action at the step S142. The air cleaner 28 may be equipped with at least one of a filtering device, which removes particles including pollen and PM 2.5 and microorganisms to purify the air, and a disinfecting device such as a UV lamp and an ozone generator, which kills or inactivates microorganism. The processor 32 may also activate a biological information acquisition unit 26 to collect additional information of the passenger and accurately determine the infection risk of the next passenger. The additional information collected by the biological information may include, for example, heart rate (HR), respiratory rate (RR), blood pressure (BP), body temperature (BT) and oxygen saturation ($SpO_2$).

At the step S142, the processor 32 may control the above-described ventilation status of the space. The processor 32 may, for example, turn the air conditioner on or off. The processor 32 may, for example, control the intensity of the air conditioner. The processor 32 may, for example, control the airflow of the air conditioner. The processor 32 may, for example, control the operation mode of the air conditioner. The processor 32 may, for example, switch recirculation of air on or off. The processor 32 may, for example control opening and closing of windows provided in the space.

Figure 10:
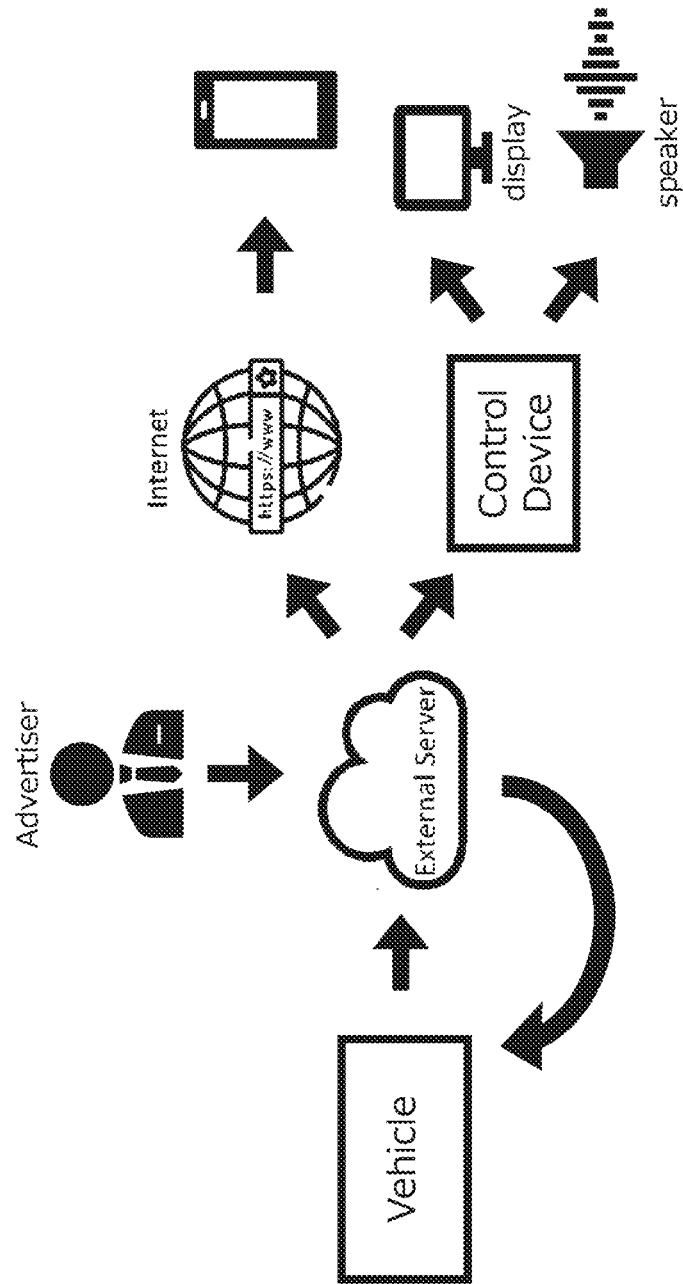
FIG. 10 illustrates an example of data related to an advertisement or data related to a warning being transmitted in the system according to the present embodiment.

At the step S142, the processor 32 may deliver an advertisement promoting the sale of a particular product to the user (for example, a taxi passenger) based on the infection risk information for the user. The advertisement may be delivered by a display, a speaker, or SNS as shown in FIG. 10. The processor 32 may, for example, cause the display to display a warning, for a manager of the space (for example, a car attendant who passes out hot towels or sells refreshments in a train, or a cabin attendant (CA) who provides various services to passengers in an airplane cabin), to encourage the user (for example, a train passenger or an airplane passenger) to apply a particular product based on the infection risk information for the user. The display is not particularly limited and may, for example, be a liquid crystal display or an organic electro-luminescence (EL) display.

For example, an advertisement promoting the sale of cold medicine or masks, such as, "How about some cold medicine?" or "Would you like to buy a mask?", may be displayed to the passenger of a taxi on a display mounted in the taxi. A warning such as, "Someone is coughing. Hand out masks to the passengers around the coughing person" may be displayed to the car attendant or CA on a display mounted in a train or an airplane to encourage a user who is coughing on the train or a user who is coughing on the airplane to wear a mask.

Specifically, as shown in FIG. 10, the processor 32 may transmit information related to an advertisement prompting the user to purchase a particular product, and information related to a warning prompting the user to wear a particular product, to the external server. The processor 32 may also transmit information related to an advertisement prompting the user to purchase a particular product, and information related to a warning prompting the user to wear a particular product, to a mobile phone via the external server and the Internet. The processor 32 may also transmit information related to an advertisement prompting the user to purchase a particular product, and information related to a warning prompting the user to wear a particular product, to an output interface via the external server and a control device. For example, when the output interface is a display, the display is controlled by the control device and displays these pieces of information. For example, when the output interface is a speaker, the speaker is controlled by the control device and outputs these pieces of information as audio. The configuration of the control device is not particularly limited as long as the control device can control the output interface. The control device may, for example, be a central processing unit (CPU) mounted in a PC, smartphone, or the like.

Alternatively, information related to an advertisement prompting the user to purchase a particular product, information related to a warning prompting the user to wear a particular product, and the like may be registered in the external server by an advertiser, a manager, or the like. For example, the advertiser may store, in the external server, information related to an advertisement prompting the user to purchase a particular product. For example, the manager may store, in the external server, information related to a warning prompting the user to wear a particular product. The external server can transmit these pieces of information to the processor 32, and the processor 32 can store these pieces of information received from the external server.

The communication frequency between the processor 32 and the external server 50 and types of the information to be transmitted to the external server 50 may be modified at the step S144. For example, at a normal state, the communication frequency is set to be low in order to reduce the cost associated with the communication and/or loads of the vehicle terminal 30 and the external server 50. When the infection risk of the passenger P is higher, the communication frequency is set to be higher so that a health condition of the passenger can be tracked more frequently. In addition or as an alternative, the additional information collected by the biological information acquisition unit 26 may be integrated into the information to be transmitted to the external server 50 so that the health condition of the passenger can be evaluated more accurately.

At the step S144, the processor 32 may control the communication frequency between the processor 32 and the external server 50 in accordance with actions by the manager. Examples of actions by the manager include the manager pressing a button a predetermined number of times, the manager coughing in a predetermined pattern, and the manager outputting audio data at a predetermined rhythm. The predetermined number of times, the predetermined pattern, the predetermined rhythm, and the like may be set in advance and stored in the memory. The audio data may be the acoustic event or may be newly generated audio data.

For example, the processor 32 may increase the communication frequency between the processor 32 and the external server 50 if a taxi driver slaps the steering wheel three times when a suspiciously behaving passenger boards the taxi. This enables the taxi driver to notify an external destination of the danger and receive external help without making the suspiciously behaving passenger aware.

Then, the processor 32 transmits, at the step S150, the infection risk information and/or the vehicle compartment contamination information via the network interface 40 over the network to the external server 50. The external server 50 forwards all or a part of the information to the external user terminal 60.

The external server 50 may utilize the information received from the processor 32 in various ways. For example, the external server 50 may accumulate the data from the vehicles over the time and monitor a clue of the outbreak of the respiratory disease and/or allergy. The external server 50 may also visualize the infection risk information from multiple vehicles on a map, and provide the map to drivers or send a warning to a vehicle driving within or toward an area where the infection risk is considered as high via the network. The information and the map may be provided to other service providers and governmental agencies such as the CDC.

At the step S150, in the case of the system and method according to the present disclosure being applied to management of shared vehicles, the processor 32 may transmit the infection risk information for the user and countermeasure information to notify people present at the destination.

For example, when the destination of a taxi or a bus is an amusement park, the processor 32 may notify the visitors in the amusement park that, "Someone with a high infection risk will be arriving shortly. Everyone, please wear a mask." When the destination of an ambulance is a hospital, for example, the processor 32 may notify the doctors and nurses in the hospital that, "A patient with a high infection risk will be arriving shortly. Please be cautious when treating the patient."

At the step S150, the processor 32 may transmit the infection risk information to the external server, the external user terminal, or the third party to notify the user and people other than the user who are located around the user of the infection risk information for the user. For example, the processor 32 may cause the display to display an indication that the infection risk of a predetermined user is high or that the infection risk of a predetermined user is low. For example, the processor 32 may cause an audio output interface to output an indication that the infection risk of a predetermined user is high or that the infection risk of a predetermined user is low. The people other than the user who are located around the user can thereby feel a sense of relief, and the people other than the user who are located around the user can be encouraged to be cautious.

For example, the processor 32 may cause a display mounted in a train to display a screen indicating, "A passenger with a high infection risk is located in car number three. Therefore, the infection risk of car number three is high" in order to notify all the passengers of the train of the infection risk information of a passenger with a high infection risk. For example, the processor 32 may cause speakers in a school to output audio indicating that, "A student with a high infection risk is located in the classroom of class number two. Therefore, the infection risk of class number two is high" to notify all of the students studying in the school of the infection risk information of a student with a high infection risk.

At the step S150, the processor 32 may, based on the infection risk information of the user, transmitting instruction to notify the manager of a space (such as a taxi driver or a person in charge at the institution that operates the space) to improve the ventilation status of the space.

For example, when the infection risk of a taxi passenger is low, yet a respiratory disease symptom of the passenger is detected at a high frequency, the processor 32 may predict that the environment inside the taxi is growing worse and notify the taxi driver that, "The cabin of the taxi is dusty. Please improve the ventilation status inside the taxi immediately."

For example, when the infection risk of a patient waiting in the waiting room of a hospital is low, yet a respiratory disease symptom of the patient waiting in the waiting room of the hospital is detected at a high frequency, the processor 32 may predict that the environment inside the waiting room of the hospital is growing worse and instruct the person in charge at the institution that operates the hospital to "Let some outside air into the waiting room of the hospital to improve the ventilation status."

The manager can thereby easily judge whether the infection risk of the patient is actually high, or whether the respiratory disease symptom of the patient is presenting due to a poor environment inside the space.

At the step S150, the processor 32 may rate the user based on statement related to physical condition of the user (for example, responses from the user to questions related to physical condition) and on the infection risk information for the user.

For example, when a passenger responds "no continued coughing and sneezing" to a questionnaire before boarding, yet a respiratory disease symptom of the passenger is detected at a high frequency (that is, when the processor 32 detects that the infection risk of the passenger is high), the processor 32 may judge that the passenger has lied and may give the passenger a low rate.

For example, when a passenger responds "no continued coughing and sneezing" to a questionnaire before boarding, and a respiratory disease symptom of the passenger is detected at a low frequency (that is, when the processor 32 detects that the infection risk of the passenger is low), the processor 32 may judge that the passenger has responded honestly and may give the passenger a high rate.

Since a user who responds honestly receives a high assessment, whereas a user who lies receives a low assessment, a user's desire to obtain a high assessment can be encouraged. The number of users who respond honestly for the manager can therefore be increased. This enables the manager to take appropriate measures for users based on valid information.

At the step S150, when the "space" is a particularly wide space, the processor 32 may transmit information the degree of risk of area within the space to notify the user of which location has a high infection risk or which location has a low infection risk within the wide space. Examples of a wide space include an airplane, a school, a bus, an apartment, and a hotel.

For example, the processor 32 may notify the user that the infection risk is high in first class seats but low in regular class seats inside an airplane. For example, the processor 32 may notify the user that the infection risk is high at the third bathroom from the right but is low at other bathrooms among a plurality of bathrooms provided in a hotel by image using a display. The processor 32 may also notify the user that which seats are at high infection risk as shown in FIG. 11.

The processor 32 may, for example, display a screen indicating the risk degree of the "space" on the display. Specifically, the processor 32 may display a screen indicating the risk degree of the seats inside an airplane on the display of a PC mounted in the airplane, as shown in FIG. 11. The risk degree of the seats inside the airplane can be represented by a change in form. For example, the risk degree of the seats inside the airplane can be represented by a change in color.

Figure 11:
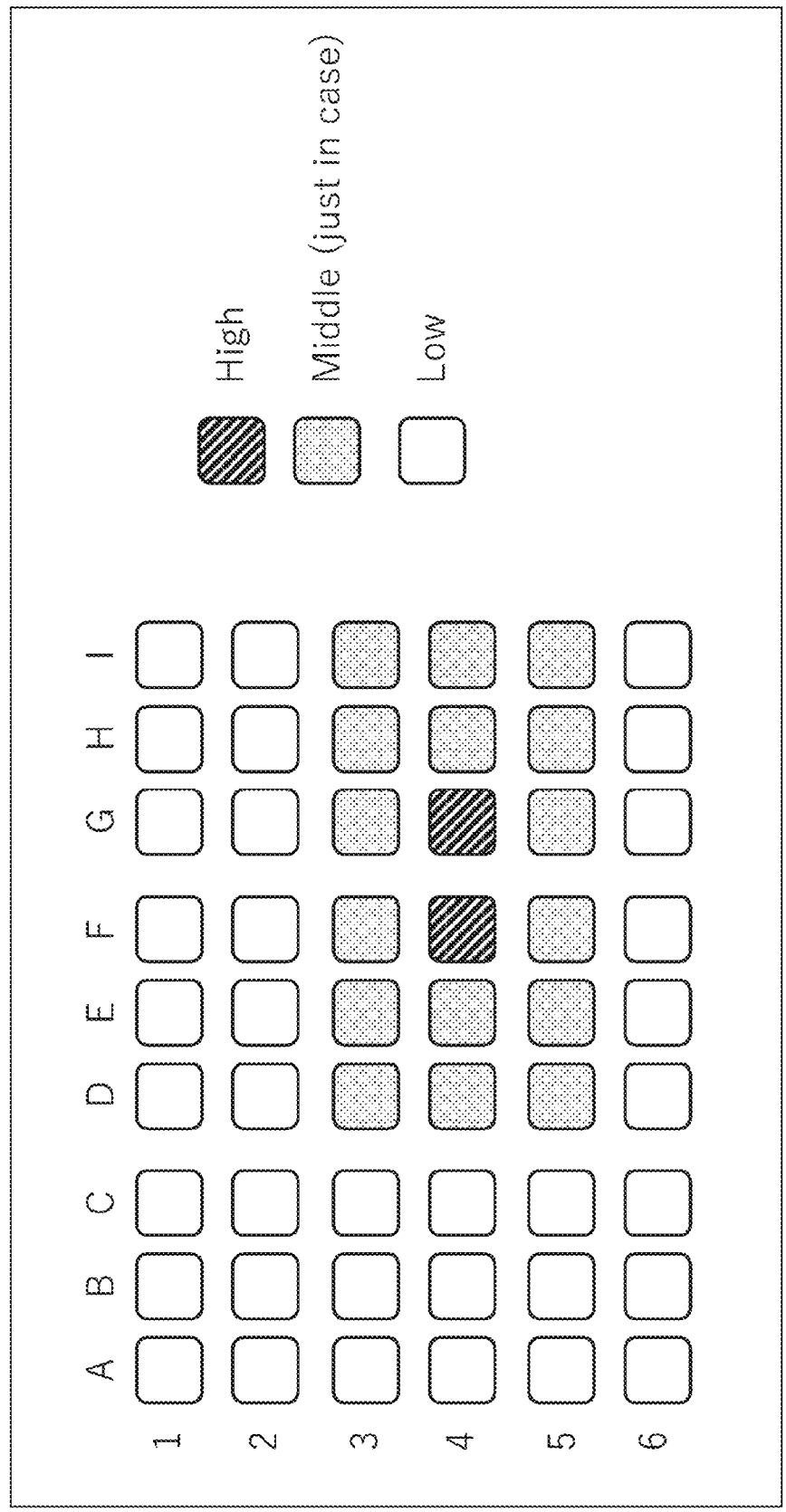
FIG. 11 illustrates an example of a screen indicating the risk degree of seats inside an airplane.

FIG. 11 illustrates an example of a screen indicating the risk degree of the seats inside an airplane, but the screen indicating the risk degree of the "space" is not limited to this example. The screen indicating the risk degree of the "space" may be a screen indicating the risk degree of any type of facility, such as a screen indicating the risk degree of the seats inside a ship, or a screen indicating the risk degree of the seats inside a waiting room.

In the screen indicating the risk degree of the seats inside the airplane, as shown in FIG. 11, the display of seat 4F and seat 4G in a diagonal stripe pattern, for example, indicates that seat 4F and seat 4G are seats with a "high" risk degree among the seats inside the airplane. In the screen indicating the risk degree of the seats inside the airplane, the display of seat 3D, seat 3E, seat 3F, seat 3G, seat 3H, seat 3I, seat 4D, seat 4E, seat 4H, seat 4I, seat 5D, seat 5E, seat 5F, seat 5G, seat 5H, and seat 5I in a dotted pattern, for example, indicates that seat 3D, seat 3E, seat 3F, seat 3G, seat 3H, seat 3I, seat 4D, seat 4E, seat 4H, seat 4I, seat 5D, seat 5E, seat 5F, seat 5G, seat 5H, and seat 5I are seats with a "middle" risk degree among the seats inside the airplane. In the screen indicating the risk degree of the seats inside the airplane, the display of the seats other than these seats with no pattern, for example, indicates that the seats other than these seats are seats with a "low" risk degree among the seats inside the airplane. The risk degree may be defined in association with the likelihood (risk) of an infection of a next user expected to use the seat. For example, less than 1% may be defined as "low", 1% or more and less than 20% may be defined as "middle", and more than 20% may be defined as "high". The risk degree may also be defined in association with the necessity of a disinfectant procedure prior to a next use of the seat.

By the screen indicating the risk degree of the seats inside the airplane thus being displayed on the display, the manager (such as the CA who provides various services to passengers in the airplane) can instantly determine which seats have a high infection risk and which seats have a low infection risk.

The risk degree of the seats inside the airplane can also be represented by a change in color. In the screen indicating the risk degree of the seats inside the airplane, the display of seat 4F and seat 4G in red, for example, may indicate that seat 4F and seat 4G are seats with a "high" risk degree among the seats inside the airplane. In the screen indicating the risk degree of the seats inside the airplane, the display of seat 3D, seat 3E, seat 3F, seat 3G, seat 3H, seat 3I, seat 4D, seat 4E, seat 4H, seat 4I, seat 5D, seat 5E, seat 5F, seat 5G, seat 5H, and seat 5I in yellow, for example, may indicate that seat 3D, seat 3E, seat 3F, seat 3G, seat 3H, seat 3I, seat 4D, seat 4E, seat 4H, seat 4I, seat 5D, seat 5E, seat 5F, seat 5G, seat 5H, and seat 5I are seats with a "middle" risk degree among the seats inside the airplane. In the screen indicating the risk degree of the seats inside the airplane, the display of the seats other than these seats in blue, for example, may indicate that the seats other than these seats are seats with a "low" risk degree among the seats inside the airplane.

Figure 6:
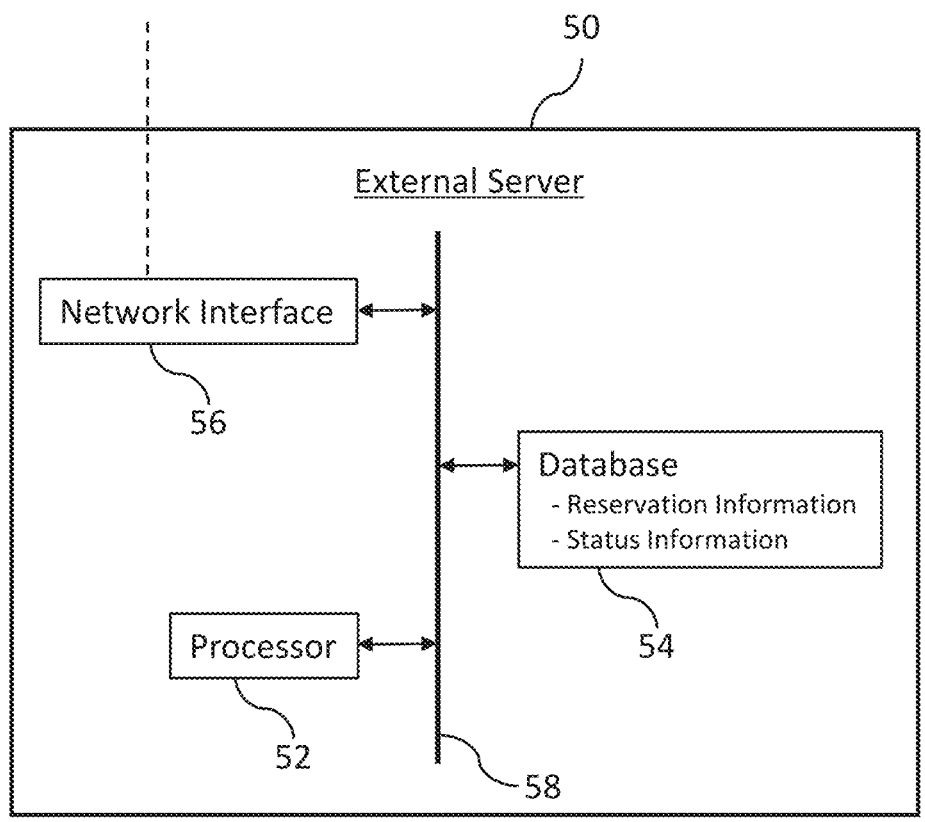
FIG. 6 is a block diagram showing an example of the external server used in the system for managing shared vehicles according to one embodiment of the present disclosure.

In one embodiment shown in FIG. 6, the external server 50 utilizes the information to manage an entire fleet schedule. The external server 50 includes a processor 52, a database 54 and a network interface 56 which are connected with each other via a bus 58. The database 54 stores reservation information and status information of the shared vehicles managed by the system 10.

Figure 7:
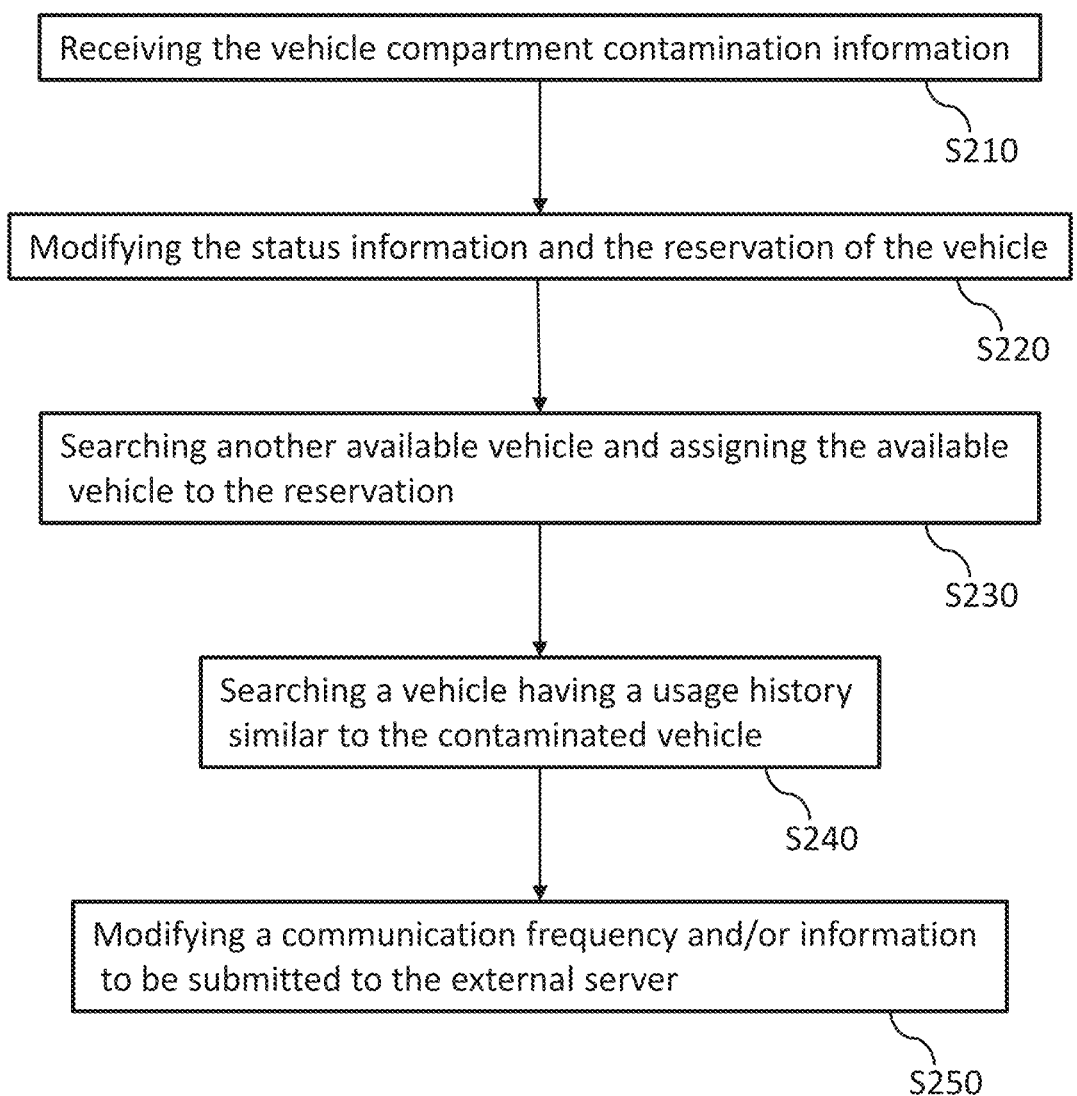
FIG. 7 is a flowchart showing steps implemented by the external server according to another embodiment of the present disclosure.
Figure 8:
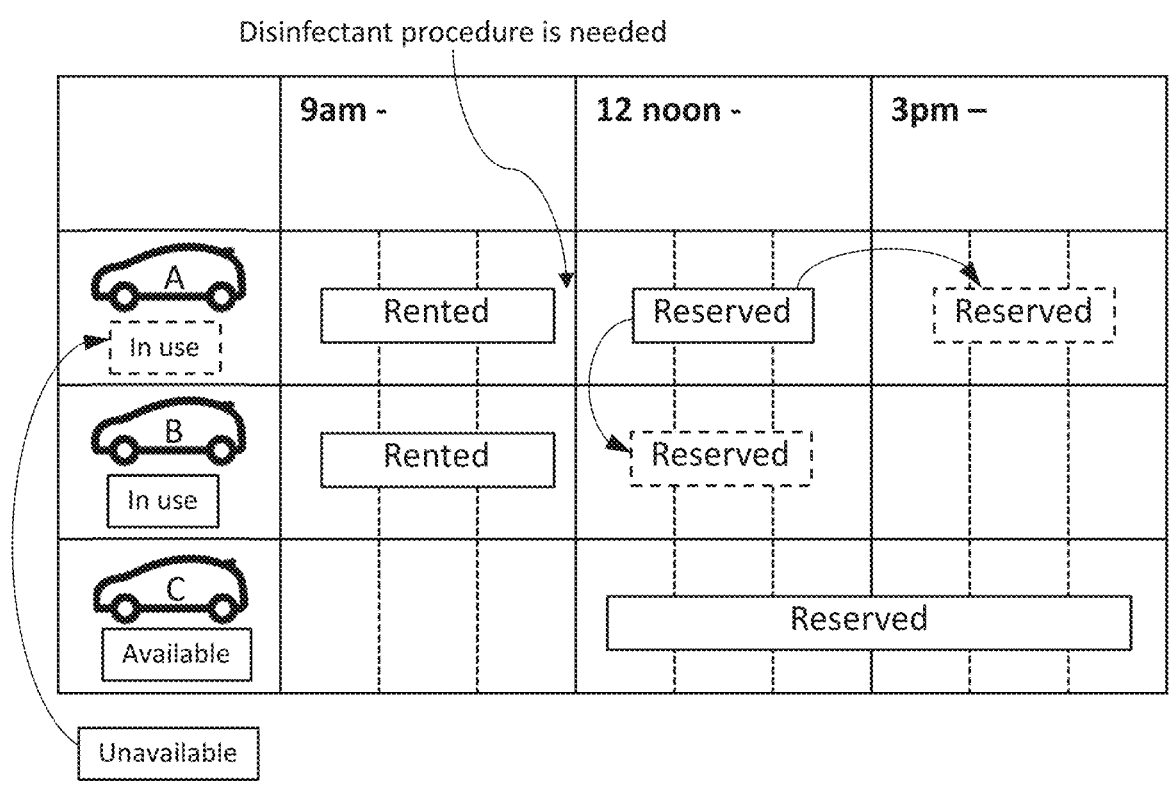
FIG. 8 is an example of status information and reservation information stored in a database.

Referring now to FIGS. 7 and 8, a procedure to manage the fleet schedule is discussed. FIG. 7 is a flowchart showing steps implemented by the external server and FIG. 8 is an example of the fleet schedule including the status information and the reservation information stored in the database 54. In this embodiment, the external server 50 is managing the schedules of vehicles A, B and C.

The processor 52 receives the vehicle compartment contamination information from the vehicle terminal 30 via the network interface 56 over the network (S210). Depending on the content of the vehicle compartment contamination information, the processor 52 modifies the status information of the vehicle 20 to reflect the vehicle compartment contamination information stored in the database 54 (S220). For example, when the vehicle compartment contamination information from the vehicle A indicates that the disinfectant procedure is needed, the processor 52 changes the status information of the vehicle A from "In use" to "Unavailable", which will prohibit any future reservations from being assigned to the vehicle A. Then, the processor 52 looks up the reservation information of the vehicle A. In this case, a reservation already exists in a time slot between 12 noon and 3 pm. Since the vehicle A needs to be disinfected prior to the next use and will be unavailable until the disinfectant procedure is completed, this reservation must be changed. Thus, the processor 52 searches an available vehicle in this time slot from the fleet schedule. As the vehicle B is available in this time slot, the processor 52 reassigns the reservation to the vehicle B and move the reservation information from the vehicle A to the vehicle B (S230). Alternatively, the processor 52 reschedule the reservation to another time slot (e.g., between 3 pm and 6 pm) to secure sufficient time to complete the disinfectant procedure. Upon receiving a report of a completion of the disinfectant procedure, the processor updates the vehicle compartment contamination information from "Unavailable" to "Available" so as to indicate that the vehicle is clean.

Optionally, the external server 50 may also search any vehicle having a usage history similar to that of the vehicle 20 (S240). If such a vehicle having the similar usage history is found, and the infection risk of such a vehicle is high, the external server 50 may send a command to the processor 32 to modify the communication frequency and/or the information to be transmitted to the external server 50 regardless of the current status of the infection risk (S250).

Optionally, the external server 50 may send a notification to the external user terminal 60. The notification may include, for example, an order for the disinfectant procedure and an updated reservation. The external server 50 may also send such a notification to a contractor providing a disinfectant service or a customer having the reservation via an email or a text message.

Figure 12:
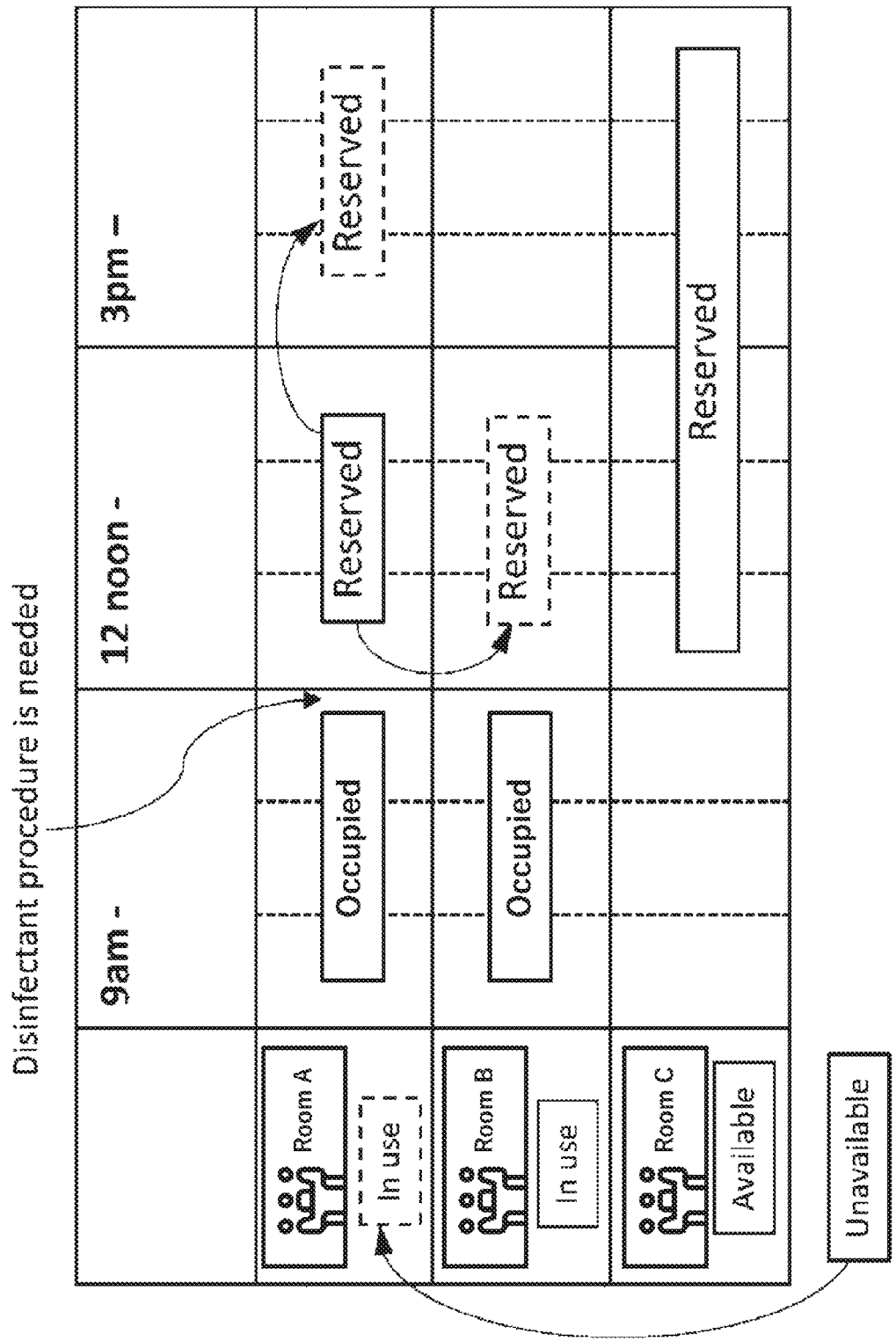
FIG. 12 illustrates an example of status information and reservation information stored in a database provided in an external server according to the present embodiment.

The external server can not only store the fleet schedule, as described above, but can also store a facility schedule. FIG. 12 illustrates an example of the status information and reservation information stored in the database 54. In FIG. 12, the facility is described as having three rooms, such as room A, room B, and room C. The time slots are described as including three time slots, such as between 9 am and 12 noon, between 12 noon and 3 pm, and between 3 pm and 6 pm.

The processor 52 receives contamination information for room A, contamination information for room B, and contamination information for room C via the network interface 56. Based on the contamination information for room A, the contamination information for room B, and the contamination information for room C, the processor 52 changes the status information for room A, the status information for room B, and the status information for room C.

For example, upon receiving information indicating that a disinfectant procedure is needed as the contamination information for room A between 9 am and 12 noon, the processor 52 changes the status information for room A from "In use" to "Unavailable". For example, upon receiving information indicating that a disinfectant procedure is not needed as the contamination information for room B between 9 am and 12 noon, the processor 52 leaves the status information for room B as "In use", with no change. For example, upon receiving information indicating that a disinfectant procedure is not needed as the contamination information for room C between 9 am and 12 noon, the processor 52 leaves the status information for room B as "Available", with no change.

Next, in addition to the contamination information for room A, the contamination information for room B, and the contamination information for room C, the processor 52 searches, based on the facility schedule, for reservation information for another room available in the same time slot and reservation information for the same room available in a different time slot. Based on these pieces of reservation information, the processor 52 then changes the reservation information for room A, the reservation information for room B, or the reservation information for room C.

For example, when the processor 52 determines that between 12 noon and 3 pm, room A cannot be used, room B can be used, and room C cannot be used, the processor 52 changes reservation information for room A indicating that "room A is reserved between 12 noon and 3 pm" to reservation information for room B indicating that "room B is reserved between 12 noon and 3 pm". For example, when the processor 52 determines that between 3 pm and 6 pm, room A can be used, room B can be used, and room C cannot be used, the processor 52 changes reservation information for room A indicating that "room A is reserved between 12 noon and 3 pm" to reservation information for room A indicating that "room A is reserved between 3 pm and 6 pm". When the processor 52 determines that between 3 pm and 6 pm, room A can be used, room B can be used, and room C cannot be used, the processor 52 can also change reservation information for room A indicating that "room A is reserved between 12 noon and 3 pm" to reservation information for room B indicating that "room B is reserved between 3 pm and 6 pm".

By the processor 52 thus appropriately managing each room based on the contamination information for room A, the contamination information for room B, the contamination information for room C, and information related to the facility schedule, the user can use only a room for which a disinfectant procedure is not needed, without using a room for which a disinfectant procedure is needed, during an appropriate time slot. A system 10 for managing a shared facility that can ensure the safety of users of the facility, without harming the users' health, can thereby be achieved.

Figure 13:
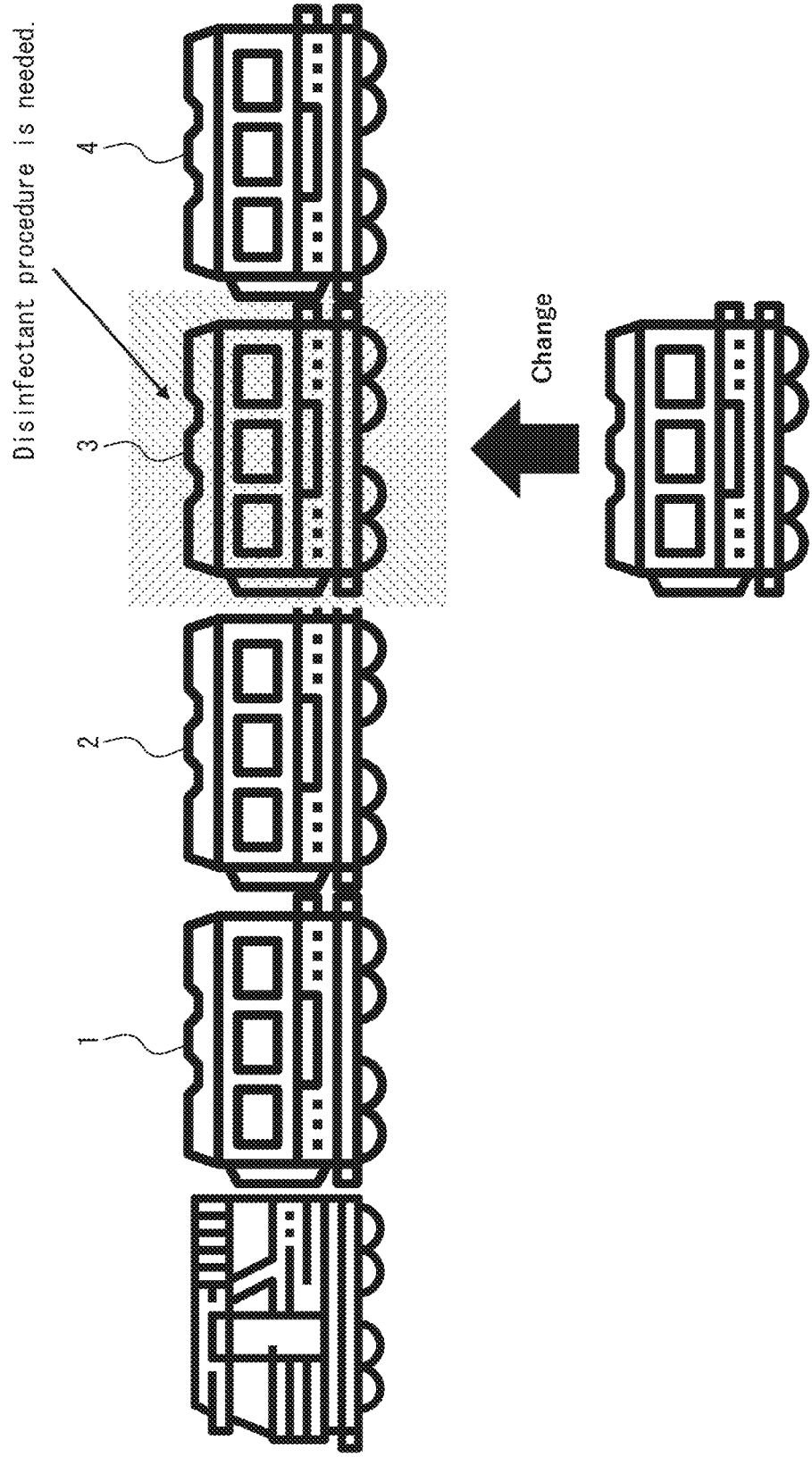
FIG. 13 illustrates an example of processing for a vehicle with a high infection risk in the system according to the present embodiment.

As shown in FIG. 13, a vehicle for which "a disinfectant procedure is needed" may be changed with another vehicle as needed.

When the processor 52 receives information indicating that "a disinfectant procedure is not needed" for the first vehicle, the second vehicle, and the fourth vehicle, and receives information indicating that "a disinfectant procedure is needed" for the third vehicle, the processor 52 may determine to change the third vehicle with a new vehicle. The processor 52 may then display the determination result, i.e. to change the third vehicle with a new vehicle, on the display of a PC mounted in the lead vehicle, for example.

As shown in FIG. 14, an airplane for which "a disinfectant procedure is needed" may undergo a ship change with another airplane as needed.

When the processor 52 receives information indicating that "a disinfectant procedure is needed" for the first airplane and receives information indicating that "a disinfectant procedure is not needed" for the second airplane and the third airplane, the processor 52 may determine that the first airplane is to undergo a ship change with a new airplane and may determine that the time required for such a ship change process is 1.5 hours. The processor 52 may then display the determination result, i.e. that the first airplane is to undergo a ship change with a new airplane, and the processing time required for the ship change process on the display of a PC provided in an operation control center, for example.

As shown in FIG. 14, an airplane for which "a disinfectant procedure is needed" may undergo disinfection as needed.

When the processor 52 receives information indicating that "a disinfectant procedure is needed" for the first airplane and receives information indicating that "a disinfectant procedure is not needed" for the second airplane and the third airplane, the processor 52 may determine that the first airplane is to undergo disinfection and may determine that the time required for such a disinfection process is 2 hours. The processor 52 may then display the determination result, i.e. that the first airplane is to undergo disinfection, and the processing time required for the disinfection process on the display of a PC provided in an operation control center, for example.

As shown in FIG. 14, an airplane for which "a disinfectant procedure is needed" may be changed with another airplane that arrives by ferry flight from another airport.

When the processor 52 receives information indicating that "a disinfectant procedure is needed" for the first airplane and receives information indicating that "a disinfectant procedure is not needed" for the second airplane and the third airplane, the processor 52 may determine that the first airplane is to be changed with another airplane that arrives by ferry flight from another airport and may determine that the time required for such a ferry flight process is a predetermined time. For example, the processor 52 may determine that the first airplane is to be changed with a new airplane that arrives from airport A by ferry flight and may determine that the time required for such a ferry flight process is 3 hours. For example, the processor 52 may determine that the first airplane is to be changed with a new airplane that arrives from airport B by ferry flight and may determine that the time required for such a ferry flight process is 4 hours.

The processor 52 may then display the determination result, i.e. that the first airplane is to be changed with a new airplane that arrives from another airport by ferry flight, and the processing time required for the ferry flight process on the display of a PC provided in an operation control center, for example. For example, the processor 52 may display, on the display, that the time required for the ferry flight process for the first airplane to be changed with a new airplane that arrives from airport A by ferry flight is 3 hours. For example, the processor 52 may display, on the display, that the time required for the ferry flight process for the first airplane to be changed with a new airplane that arrives from airport B by ferry flight is 4 hours.

The type of process performed on the airplane for which "a disinfectant procedure is needed" and the processing time for performing the process on the airplane for which "a disinfectant procedure is needed" are not particularly limited. The type of process and the processing time may be set in advance by the controller or may be set freely by the manager or the like.

The matter set forth in the foregoing description and accompanying drawings is offered by way of illustration only and not as a limitation. While particular embodiments have been shown and described, it will be apparent to those skilled in the art that changes and modifications may be made without departing from the broader aspects of applicant's contribution.

For example, the above-discussed steps may be stored in computer readable non-transitory storage medium as a series of operations or a program related to the operations that is executed by a computer system or other hardware capable of executing the program. In addition, the operations may be performed by a dedicated circuit implementing the program codes, a logic block or a program module executed by one or more processors, or the like.

Moreover, all the steps shown in FIGS. 4 and 5 are implemented by the processor 32 on the vehicle terminal 30 in the above-discussed embodiments, all or some of these steps may be implemented by the external server 50.

Although the present disclosure is described mainly with respect to a vehicle managing system concerning the rental/shared car facility, the application of the present invention is not limited to such a car rental business. The present invention is also applicable to taxicab fleet management, ride-sharing fleet management, delivery truck fleet management, and other vehicle fleet management industries.

The actual scope of the protection sought is intended to be defined in the following claims when viewed in their proper perspective based on the prior art.

The invention claimed is:

1. A system for managing facilities, the system comprising
   an acoustic event detector including an acoustic sensor for detecting an acoustic event in a compartment of a facility,
   a facility terminal electrically connected to the acoustic event detector, and
   an external server communicating with the facility terminal via a network,
   wherein at least one of the facility terminal and the external server comprises a processor,
   the processor is configured to implement the steps of:
      extracting a respiratory disease symptom of a user in the facility from the detected acoustic event;
      assessing at least one of intensity, frequency, and duration of the respiratory disease symptom of the user to determine a severity of the symptom;
      assessing a ventilation status of the facility indicated by a concentration of carbon dioxide;
      generating infection risk information associated with an infection risk of a next user expected to use the facility from the severity of the symptom and the ventilation status of the facility;
      transmitting the infection risk information to at least one of an external user terminal, the external server, and a third party via the network; and
      transmitting instruction to improve the ventilation status of the facility to at least one of the external server, the facility terminal, the external user terminal, and the third party via the network based on the infection risk information, and
   the transmitting the instruction comprises transmitting the instruction when the severity of the symptom is high while the infection risk is low.

2. The system according to claim 1, wherein the acoustic sensor captures acoustic sound,
   and the processor is further configured to implement the step of:
   transmitting the acoustic data to at least one of the external user terminal, the external server, and the third party via the network.

3. The system according to claim 1, wherein the processor is further configured to implement the step of:
   delivering an advertisement to at least one of the external server, the facility terminal, the external user terminal, and the third party via the network based on the infection risk information.

4. The system according to claim 1, wherein the processor is further configured to implement the step of:
   rating the user based on statement related to physical condition of the user and on the infection risk information for the user.

5. The system according to claim 1, wherein the processor is further configured to implement the step of:
   transmitting information indicating the degree of risk of area within the facility to at least one of the external server, the facility terminal, the external user terminal, and the third party via the network based on the infection risk information.

6. The system according to claim 1, the processor is further configured to implement the step of:
   transmitting countermeasure information to at least one of the external server, the facility terminal, the external user terminal, and the third party via the network based on the infection risk information.

7. The system according to claim 1, wherein the processor is further configured to implement the step of:
   modifying at least one of a communication frequency and information to be transmitted to at least one of the external server, the facility terminal, the external user terminal, and the third party via the network.

8. The system according to claim 1, further comprising an air cleaner in the facility,
   wherein the processor is further configured to implement the step of:
   controlling the air cleaner on the basis of a frequency of occurrence of the respiratory disease symptom.

9. The system according to claim 1, wherein the processor is further configured to implement the steps of:
generating facility compartment contamination information indicating a necessity of a disinfectant procedure prior to a next use of the facility based on the infection risk information, and
transmitting the facility compartment contamination information to at least one of the external server, the facility terminal, the external user terminal, and the third party via the network.

10. The system according to claim 1, wherein the external server searches a potentially contaminated facility having a usage history similar to that of the facility determined as high infection risk, and modifies at least one of a communication frequency and information to be transmitted to at least one of the external server, the facility terminal, the external user terminal, and the third party via the network.

11. A method for managing facilities, the method comprising the steps of:
detecting an acoustic event in a compartment of a facility;
extracting a respiratory disease symptom of a user in the facility from the detected acoustic event;
assessing at least one of intensity, frequency, and duration of the respiratory disease symptom of the user to determine a severity of the symptom;
assessing a ventilation status of the facility indicated by a concentration of carbon dioxide;
generating infection risk information associated with an infection risk of a next user expected to use the facility from the severity of the symptom and the ventilation status of the facility;
transmitting the infection risk information to at least one of an external user terminal, the external server, and a third party via a network; and
transmitting instruction to improve the ventilation status of the facility to at least one of the external server, the facility terminal, the external user terminal, and the third party via the network based on the infection risk information, and
wherein the transmitting the instruction comprises transmitting the instruction when the severity of the symptom is high while the infection risk is low.

12. The method according to claim 11, further comprising the step of:
transmitting the acoustic data to at least one of the external user terminal, the external server, and the third party via the network.

13. The method according to claim 11, further comprising the step of:
delivering an advertisement to at least one of the external server, the facility terminal, the external user terminal, and the third party via the network based on the infection risk information.

14. The method according to claim 11, further comprising the step of:
rating the user based on statement related to physical condition of the user and on the infection risk information for the user.

15. The method according to claim 11, further comprising the step of:
transmitting information indicating the degree of risk of area within the facility to at least one of the external server, the facility terminal, the external user terminal, and the third party via the network based on the infection risk information.

16. The method according to claim 11, further comprising the step of:
transmitting countermeasure information to at least one of the external server, the facility terminal, the external user terminal, and the third party via the network based on the infection risk information.

17. The method according to claim 11, further comprising the step of:
modifying at least one of a communication frequency and information to be transmitted to at least one of the external server, the facility terminal, the external user terminal, and the third party via the network.

18. The method according to claim 11, further comprising the step of:
controlling an air cleaner on the basis of a frequency of occurrence of the respiratory disease symptom.

19. The method according to claim 11, further comprising the step of:
generating facility compartment contamination information indicating a necessity of a disinfectant procedure prior to a next use of the facility based on the infection risk information, and
transmitting the facility compartment contamination information to at least one of the external server, the facility terminal, the external user terminal, and the third party via the network.

20. The method according to claim 11, further comprising the steps of:
searching a potentially contaminated facility having a usage history similar to that of the facility determined as high infection risk, and
modifying at least one of a communication frequency and information to be transmitted to at least one of the external server, the facility terminal, the external user terminal, and the third party via the network.

21. A system for managing facilities, the system comprising
an acoustic event detector including an acoustic sensor for detecting an acoustic event in a compartment of a facility,
a facility terminal electrically connected to the acoustic event detector, and
an external server communicating with the facility terminal via a network,
wherein at least one of the facility terminal and the external server comprises a processor,
the processor is configured to implement the steps of:
extracting a respiratory disease symptom of a user in the facility from the detected acoustic event;
assessing at least one of intensity, frequency, and duration of the respiratory disease symptom of the user to determine a severity of the symptom;
assessing a ventilation status of the facility indicated by a concentration of carbon dioxide;
generating infection risk information associated with an infection risk of a next user expected to use the facility from the severity of the symptom and the ventilation status of the facility; and
transmitting the infection risk information to at least one of an external user terminal, the external server, and a third party via the network, and
the processor is configured to change a frequency of the transmitting the infection risk information in accordance with the infection risk.

* * * * *